(12) United States Patent
Bhatnagar

(10) Patent No.: US 10,603,418 B2
(45) Date of Patent: Mar. 31, 2020

(54) EXPRESSION OF BREAST MILK VIA AUTOMATED METHODS FOR MANAGING PUMPED BREAST MILK, LACTATION ANALYTICS AND PATIENT ENGAGEMENT

(71) Applicant: Keriton, LLC, Philadelphia, PA (US)

(72) Inventor: Vidur S. Bhatnagar, Philadelphia, PA (US)

(73) Assignee: KERITON, INC., Philadelphia, PA (US)

(*) Notice: Subject to any disclaimer, the term of this patent is extended or adjusted under 35 U.S.C. 154(b) by 212 days.

(21) Appl. No.: 15/616,493

(22) Filed: Jun. 7, 2017

(65) Prior Publication Data

US 2017/0354771 A1 Dec. 14, 2017

Related U.S. Application Data

(60) Provisional application No. 62/427,419, filed on Nov. 29, 2016, provisional application No. 62/347,321, filed on Jun. 8, 2016.

(51) Int. Cl.

| | | |
|---|---|---|
| *A61M 1/00* | (2006.01) | |
| *G16H 10/00* | (2018.01) | |
| *G06F 19/00* | (2018.01) | |
| *A61M 1/06* | (2006.01) | |
| *G16H 10/60* | (2018.01) | |

(Continued)

(52) U.S. Cl.
CPC .......... *A61M 1/062* (2014.02); *G06F 19/324* (2013.01); *G16H 10/60* (2018.01); *G16H 40/20* (2018.01); *G16H 40/63* (2018.01); *A61M 2205/18* (2013.01); *A61M 2205/3569* (2013.01); *A61M 2205/50* (2013.01); *A61M 2205/502* (2013.01); *A61M 2205/52* (2013.01); *A61M 2205/583* (2013.01)

(58) Field of Classification Search
CPC ....... A61M 1/062; A61M 1/06; G06F 19/324; G16H 10/60
See application file for complete search history.

(56) References Cited

U.S. PATENT DOCUMENTS

| | | |
|---|---|---|
| 8,172,129 B1 | 5/2012 | Laurenzi et al. |
| 2007/0156060 A1 | 7/2007 | Cervantes |

(Continued)

FOREIGN PATENT DOCUMENTS

WO 2015-128869 A1 9/2015

OTHER PUBLICATIONS

International Search Report and Written Opinion issued in connection with International patent application No. PCT/US2017/036366, dated Sep. 8, 2017, 16 pages.

*Primary Examiner* — William R Carpenter
(74) *Attorney, Agent, or Firm* — Duane Morris LLP

(57) ABSTRACT

An apparatus for use in a milk management system comprising a first device, wherein the first device includes a non-transitory storage medium; and a processor communicatively coupled to the non-transitory storage medium. The processor is configured to: receive first data from a second device, the first data describing milk disposed in a first container, the first container having a first identifier associated therewith; and associate the first data with a first feeding order in a data structure store in a database, the first feeding order describing a first nutrition regimen.

20 Claims, 15 Drawing Sheets

(51) Int. Cl.
  *G16H 40/20*     (2018.01)
  *G16H 40/63*     (2018.01)

(56) References Cited

U.S. PATENT DOCUMENTS

| | | | |
|---|---|---|---|
| 2008/0217391 A1* | 9/2008 | Roof | G06F 19/3462 235/375 |
| 2010/0318377 A1* | 12/2010 | Lair | G06Q 10/08 705/2 |
| 2015/0274329 A1 | 10/2015 | Aesynt | |
| 2016/0082165 A1* | 3/2016 | Alvarez | A61M 1/062 604/74 |
| 2016/0094812 A1 | 3/2016 | Chen | |
| 2017/0136160 A1* | 5/2017 | Barral | A61M 1/06 |

* cited by examiner

180

| DATABASE COLUMNS |||
|---|---|---|
| 1. Container<br>CONTAINER_ID<br>PROVIDER_ID<br>MOTHER_ID<br>VOLUME<br>BREAST_SIDE<br>PUMPED_DATE<br>CHECK_IN_DATE<br>EXPIRY DATE<br>IS_HOME_AVAILABLE<br>IS_NICU_AVAILABLE<br>IS_COLOSTRUM<br>IS_FORTIFIED<br>IS_THAWED<br>IS_HIND_MILK<br>IS_FORE_MILK<br>NUTRITION_ORDER_ID<br>... | 2. Patient<br>PATIENT_ID<br>PROVIDER_ID<br>NAME<br>ADDRESS<br>USERNAME<br>PASSWORD<br>IS_MOTHER<br>IS_DISCHARGED<br>PHOTO<br>...<br>...<br>... | 2. Practitioner<br>PRACTITIONER_ID<br>PROVIDER_ID<br>IS_NURSE<br>IS_LC<br>IS_DOCTOR<br>USERNAME<br>PASSWORD<br>...<br>...<br>... |
| 1. Workflow<br>WORKFLOW_ID<br>PROVIDER_ID<br>WORKFLOW_TYPE<br>PRACTITIONER_ID<br>PATIENT_ID<br>CONTAINER_ID<br>DATE<br>...<br>...<br>... | 1. Nutrition_order<br>NUTRITION_ORDER_ID<br>PROVIDER_ID<br>PATIENT_ID<br>REQUIRED_CALORIC_VALUE<br>FORTIFIER_TYPE<br>FORTIFIER_UNIT<br>FORTIFIER_CALORIC_VALUE<br>FORTIFIER_MILK_REQUIRED<br>FEEDING_TYPE<br>FEEDING_VOLUME<br>FEEDING_FREQUENCY<br>DATE<br>... | 1. Notification<br>NOTIFICATIONS_ID<br>PROVIDER_ID<br>PATIENT_ID<br>NOTIFICATION_CONTENT<br>NOTIFICATION_TYPE<br>IS_READ<br>DATE<br>...<br>..<br>.. |
| 1. Rule<br>RULE_ID<br>PROVIDER_ID<br>RULE_DESCRIPTION<br>RULE_CONSTRAINT<br>RULE_VALUE<br>...<br>...<br>... | 1. Provider<br>PROVIDER_ID<br>PROVIDER_NAME<br>PROVIDER_ADDRESS<br>...<br>...<br>... | 1. Patient_Engagement<br>ENGAGEMENT_ID<br>PROVIDER_ID<br>PATIENT_ID<br>ENGAGEMENT_CONTENT<br>ENGAGEMENT_TYPE<br>IS_READ<br>DATE<br>...<br>...<br>... |

FIG. 2B

EXPRESSION OF BREAST MILK VIA AUTOMATED METHODS FOR MANAGING PUMPED BREAST MILK, LACTATION ANALYTICS AND PATIENT ENGAGEMENT

CROSS-REFERENCE TO RELATED APPLICATION

This application claims priority to U.S. Provisional Patent Application Ser. No. 62/347,321 filed Jun. 8, 2016 and to U.S. Provisional Patent Application Ser. No. 62/427,419 filed Nov. 29, 2016, the entireties of which are incorporated herein by reference.

FIELD

The present disclosure generally relates to the technical field of milk management. More specifically, the present disclosure is directed to systems and methods for maintaining optimal breast milk expression flow and managing inventory, verification, and validation of milk containers.

DESCRIPTION OF THE RELATED ART

In the United States, 4 million infants are born every year. Although not all are preterm or unhealthy, it is nevertheless desirable for all of those infants to drink their mother's breast milk. A mother's breast milk protects her infant from illness and diseases by providing immunological and anti-inflammatory properties. The need for mother's breast milk is higher for a preterm infant, who is kept in a specialized neonatal intensive care unit (NICU). Constituents in breast milk protect the infant from infections to which the mother is immune, for approximately five to six months after birth. Empirically proven benefits of breast milk include shorter length of stay in the NICU, fewer readmissions, lower counts of morbidities like Necrotizing Enterocolitis, Retinopathy of Prematurity, Sepsis, etc. Thus, it is desirable to maintain a continuous flow of mother's breast milk for her infant(s).

SUMMARY OF THE INVENTION

In embodiments, an apparatus for use in a milk management system comprising a first device, wherein the first device includes a non-transitory storage medium; and a processor communicatively coupled to the non-transitory storage medium. The processor is configured to: receive first data from a second device, the first data describing milk disposed in a first container, the first container having a first identifier associated therewith; and associate the first data with a first feeding order in a data structure stored in a database, the first feeding order describing a first nutrition regimen.

In embodiments, a method for use in a milk management system comprising the steps of: receiving first data from a first device, the first data describing milk disposed in a first container, the first container having a first identifier associated therewith; and, associating the first data with a first feeding order in a data structure stored in a database, the first feeding order describing a first nutrition regimen.

In embodiments, an apparatus for use in a milk management system comprising a first device, wherein the first device includes a non-transitory storage medium; and a processor communicatively coupled to the non-transitory storage medium. The processor is configured to: cause a request to be transmitted to a second device, the request including a first container identifier; and, receive first data from the second device, the first data describing milk disposed within the first container and being associated with a first feeding order, the first feeding order describing a first nutrition regimen.

In embodiments, a method for use in a milk management system comprising the steps of: receiving a first container identifier from a first container; transmitting a request to a first device, the request including the first container identifier; and, receiving first data from the first device, the first data describing milk disposed within the first container and being associated with a first feeding order, the first feeding order describing a first nutrition regimen.

In embodiments, an apparatus for use in a milk management system comprising a first device, wherein the first device includes a user interface; a communication interface; a non-transitory storage medium; and, a processor communicatively coupled to the non-transitory storage medium, to the user interface, and to the communication interface. The processor is configured to: receive first data from the user interface, the first data including a time and date when the milk disposed in a first container was pumped, a refrigeration status of the milk disposed in the first container, and an amount of the milk disposed in the first container; and, cause the communication interface to transmit a message including the first data to a second device.

In embodiments, a method for use in a milk management system comprising the steps of: receiving first data from a user interface, the first data including a time and date when the milk disposed in a first container was pumped, a refrigeration status of the milk disposed in the first container, and an amount of the milk disposed in the first container; causing a communication interface to transmit a message including the first data to a server; and, receiving at least one notification from the server by way of the communication interface, the at least one notification including at least one of a reminder to pump additional milk and an expiration date of the milk disposed in the first container.

The foregoing and additional aspects and embodiments of the present invention will be apparent to those of ordinary skill in the art in view of the detailed description of various embodiments and/or aspects, which is made with reference to the drawings, a brief description of which is provided next.

BRIEF DESCRIPTION OF THE DRAWINGS

Various aspects of the present disclosure will be or become apparent to one with skill in the art by reference to the following detailed description when considered in connection with the accompanying exemplary non-limiting embodiments, in which:

FIG. 2B depicts an example database schema for the management of milk containers in accordance with some embodiments of the present disclosure.

DETAILED DESCRIPTION

Figure 1A:
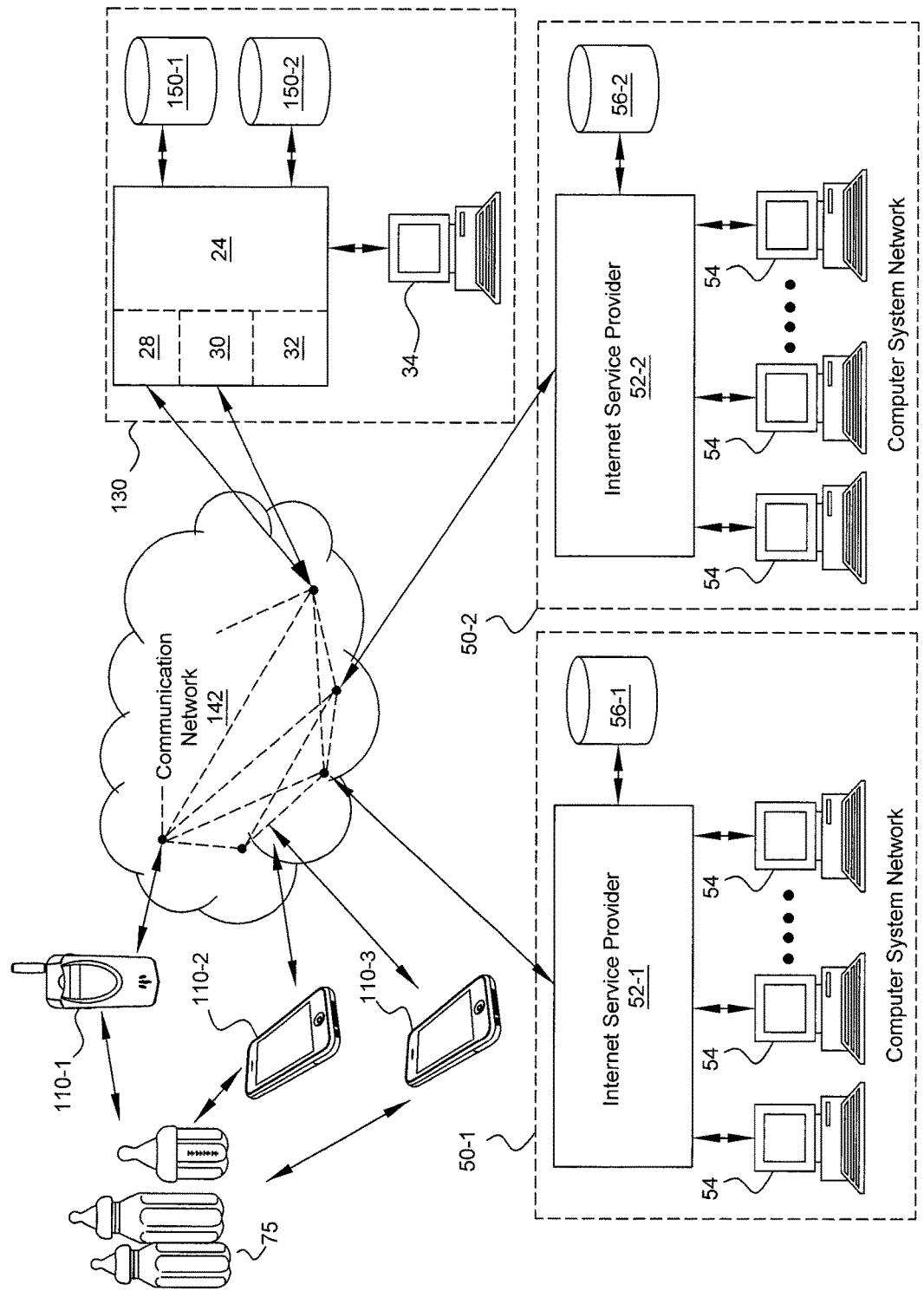
FIG. 1A illustrates one example of a system in accordance with some embodiments of the present disclosure.

This description of the exemplary embodiments is intended to be read in connection with the accompanying drawings, which are to be considered part of the entire written description. The use of the singular includes the plural unless specifically stated otherwise. The use of "or" means "and/or" unless stated otherwise. Furthermore, the use of the term "including," as well as other forms such as "includes" and "included," is not limiting. In addition, terms such as "element" or "component" encompass both elements and components comprising one unit, and elements and components that comprise more than one subunit, unless specifically stated otherwise. Additionally, the section headings used herein are for organizational purposes only, and are not to be construed as limiting the subject matter described.

The following description is provided as an enabling teaching of a representative set of examples. Many changes can be made to the embodiments described herein while still obtaining beneficial results. Some of the desired benefits discussed below can be obtained by selecting some of the features discussed herein without utilizing other features. Accordingly, many modifications and adaptations, as well as subsets of the features described herein are possible and can even be desirable in certain circumstances. Thus, the following description is provided as illustrative and is not limiting.

As used herein, use of a singular article such as "a," "an" and "the" is not intended to exclude pluralities of the article's object unless the context clearly and unambiguously dictates otherwise.

Conventional methods and processes for obtaining and providing a mother's breast milk to a child in a NICU setting (or other care unit) typically arise due to one of the following two scenarios. In the first scenario, postpartum mothers are often separated from their infant, due to the infant being admitted to a NICU. In the second scenario, infants whose mothers are physically present are often unable to latch properly onto the nipple due to underdevelopment or other such cases where a mom cannot directly feed a baby at breast. In any such situation, a mother needs to use a breast pump to express breast milk for her baby's consumption.

The mother uses the breast pump to express breast milk into several containers provided by the hospital. Ideally, a mother typically pumps 8 to 10 times a day to generate sufficient amounts of milk for her baby's consumption. This fills an average of 12 to 16 containers.

The hospital provides labels for the mother to apply onto the containers. The mother must manually write the date and timestamp of production on each of these containers. The mother then brings these containers into the NICU, where each container is checked in by a NICU nurse or attendant, by scanning the label and then manually creating the same date and time stamps noted by the mother into a database at the NICU. The nurses manually add important additional data to the label and/or database, such as: storage unit, quantity of milk, and expiration date. The expiration date varies depending on storage method (e.g., refrigeration vs. deep freezing) and is manually calculated by the nurses. The nurses then reprint labels for all containers, which now contain these additional new details and apply the new labels to the containers before placing them in storage. There might be an additional step of removing, defacing, and/or destroying the previous label to avoid potential confusion from multiple labels, such as might occur if an outer label is applied over an inner label but detaches from the inner label in the low temperature and high humidity of the storage environment.

The bottles are then placed in storage (e.g., a refrigerator or deep freezer). Subsequently, the nurses keep track of the infants' feeding orders. Before feeding, milk bottles need to be prepared based on the feeding order of the baby. To prepare a feed for the baby, the caretaker in the unit might have to transfer bottles from freezer to fridge, combine some bottles, split into new bottles, add additives such as fortifiers, etc.—all such steps require several manual validations, can change the expiration date of the milk and require relabeling the bottle. For e.g. when an additive is used, the expiration changes to 24 hours and the nurses reprint and apply new labels to the containers and/or syringes or other containers to which the milk has been transferred. Again, there may be an additional step of removing, defacing, and/or destroying the previous label. When the nurses become aware that it is approaching feeding time for a baby, the nurses locate a container of the baby's milk in storage and warm the container to room temperature. The nurses follow a two-person checking protocol, and a nurse then confirms the label on the container and a code (e.g., wristband code or incubator code) on or in proximity to the baby to ensure that the baby matches the milk. The baby is then fed upon successful verification of the match. If verification does not occur, then the nurses manually rectify the situation and locate the correct milk. Once feeding is complete, milk remaining in the container is discarded after a fixed time (e.g. an hour).

In the description above, for each mother, NICU nurses typically spend 30 to 45 minutes on every set of 12 to 16 bottles from receiving it till it is fed/emptied. For an average-sized NICU, this translates to roughly 6.5 full-time employee hours (or 13,520 hours per year) wasted on just creating manual entries and labels for the milk containers. Nurses presently have no automated scheme at the NICU to track the total available milk for feeding infants. If a mother's milk runs out, then nurses resort to donor milk or formula to feed her infant. Not all infants are suited for donor/formula feeding, which creates several health issues for the infant, such as necrotizing colitis and retinopathy of prematurity.

Lack of sufficient breast milk for the baby also means an extended length of stay for the infant in the NICU due to the infant not receiving proper nourishment. Each day in the NICU has an average cost of roughly $3,500. Sometimes mothers pump and store the bottles of milk at home, instead of bringing all the bottles to the NICU. If nurses at the NICU are running out of milk stock at the NICU, they are not aware of available milk bottles stored at home with the mother and hence resort to donor milk or formula feeds.

Current breast milk organization procedures provide that nurses manually check the expiration date of each bottle before it is used for feeding. There has previously been no system to automatically track shelf life of milk in containers, either at the NICU or at home. In addition to verifying that the milk has not expired, nurses must check each bottle before feeding the baby to make sure that it is from the associated infant's mother. The current procedures do not provide a mechanism to alert nurses of an incorrect mother-child breast milk pairing. Additionally, conventional organization procedures require manually writing sequential numbers on bottles or placing them in a particular order inside the refrigerator or deep freeze, arranged with the newest containers toward the back and the oldest toward the front.

While lactation is a natural process, pumping milk while away from the baby is an unnatural process due to the lack of stimuli such as the baby's touch and the sounds of the baby's crying. The absence of such natural stimuli makes it harder for mothers to lactate and hence produce a sufficient quantity of milk for their infants. In addition, a typical mother must pump 8 to 10 times a day to produce a sufficient quantity of milk for her infant's consumption. Due to massive emotional and physical stress, mothers often forget to do so.

Lactation experts often wish to track production patterns of mothers and intervene in a timely manner to alleviate any physical or emotional bearings that may be hampering a mother's production of breast milk. Conventional methods of tracking milk production are confined to personal tracking by the mother, which is susceptible to numerous errors and inaccuracies.

Finally, when an infant is transferred from one NICU (e.g., at a first hospital) to another NICU (e.g., at a second hospital), mothers and/or nurses must relabel all of the bottles for compatibility with the new hospital. Once an infant is discharged from a NICU, nurses need to manually find all bottles being stored for the infant being discharged and to manually delete any entries from the NICU's database. Other items that have conventionally been manually tracked by parents, nurses, and other health care professionals are the various medications and medical procedures provided to the infant while in the NICU. Tracking and ordering of donor milk has also conventionally been performed manually at the NICU.

Conventional milk management procedures and processes do not meet the needs of providing a reliable organizational and tracking system for milk containers. In addition, conventional methods of tracking do not account for infant specific needs such as suitability for donor/formula feeding. Hospitals are constantly seeking innovative ways to address the problem of insufficient milk supply. Lactation experts can assist hospitals in addressing this problem by receiving real-time notification of mothers decreasing milk supply stock. Nurses can address this problem through improved milk tracking, verification, and organization methods. Mothers can address this problem by providing a system that bridges the physical disconnect between a mother and her infant to assist in lactation while also providing valuable notification reminders to ensure that mothers pump sufficiently. Embodiments of the present disclosure address each of these areas by providing an automated milk management system that improves the expression of a mother's breast milk for her infant, for use by a unit of infant care, such as a NICU, postpartum hospital, milk donor bank, child day care, or the like.

A comprehensive automated milk management system and methods are provided in the present disclosure. As discussed throughout this specification, milk may refer to breast milk, donor milk or artificial formula based milk. The system and methods described herein, generate container specific identifiers and labels that assist caretakers (e.g., nurse, doctor, lactation consultant, daycare attendant, etc.) in the identification, verification, and validation of milk containers. Milk container may refer to any container used to store, mix, or feed milk (e.g., bottles, bags, beakers, droppers, etc.). A container identifier is an identifier used to assign a milk container to a mother, source (e.g., for donor or formula milk), feeding order, or a batch (e.g., donor or formula milk supply). The inventor has determined that the disclosed systems and methods that provide one-time labeling (e.g., no relabeling) of containers while keeping track of container identifier information (e.g., fortification, expiration, thawed, milk type) and first-in and first-out (FIFO) process flow management maximize the duration of unexpired milk. By way of example, the disclosed systems and methods provide improved tracking capability, various notification features, and real-time dashboards for caretakers to keep track of mothers' production patterns via text or visual interfaces.

The inventor has developed systems and methods for secured communications (e.g., images, videos, audio, etc.) between caretakers and mothers that digitally bridge the gap of missing stimuli. Additionally, the systems and methods provide secured communications to allow mothers to connect with caretakers. The systems and methods advantageously provide milk container identifier information, identification, verification, and validation features while permitting comprehensive tracking and communications elements to assist caretakers and mothers in maintaining breast milk supply.

System Overview

FIG. 1A depicts one example of a system 100 in which a plurality of client devices 110-1, 110-2, and 110-3 (collectively "client devices 110") are connected via communication network 142 to one or more computer system networks 50-1, 50-2 ("computer networks 50"), and to management server 130. Communication network 142 may be a wide area network ("WAN"), a local area network ("LAN"), personal area network ("PAN"), or the like. In one embodiment, communication network 142 is the Internet and client devices 110 are online. "Online" may mean connecting to or accessing source data or information from a location remote from other devices or networks coupled to communication network 142.

Management server 130 includes a processing unit 24 coupled to one or more data storage units 150-1, 150-2 (collectively referred to as "database management system 150" or "DBMS 150"). The processing unit 24, in some embodiments is configured to provide front-end graphical user interfaces ("GUI") (e.g., caretaker user GUI 28 and mother user GUI 30), and a back-end or administrative graphical user interface or portal 32 to one or more remote computers 54 or to one or more local computers 34. In some embodiments, a caretaker interface (not shown) is provided that accesses management server 130 via GUI 28. The GUIs can take the form of, for example, a webpage that is displayed using a browser program local to remote computers 54 or to one or more local computers 34. It is understood that the system 100 may be implemented on one or more computers, servers, or other computing devices. In some embodiments, the GUI may be displayed on client devices 110 via a software application. For example, system 100 may include additional servers programmed or partitioned based on permitted access to data stored in DBMS 150. As used herein, "portal" is not limited to general-purpose Internet portals, such as YAHOO! or GOOGLE but also includes GUIs that are of interest to specific, limited audiences and that provide the party access to a plurality of different kinds of related or unrelated information, links and tools as described below. "Webpage" and "website" may be used interchangeably herein.

Remote computers 54 may be part of a computer system network 50-1, 50-2 and gain access to communication network 142 through an Internet service provider ("ISP") 52-1, 52-2 ("ISPs 52"). Client devices 110 may gain access to communications network 142 through a wireless cellular communication network, a WAN hotspot, or through a wired or wireless connection with a computer as will be understood by one skilled in the art. Caretakers and mothers, as will be described below, may use remote computers 54 and/or client devices 110 to gain access to system 100.

In one embodiment, client devices 110 includes any mobile device capable of transmitting and receiving wireless signals. Examples of mobile instruments include, but are not limited to, mobile or cellular phones, personal digital assistants ("PDAs"), laptop computers, tablet computers, music players, and e-readers, to name a few possible devices.

In various embodiments, as described in further detail below, client devices 110 are configured to identify containers 75 (e.g., a imaging device to read a visual identifier, an RFID scanner to read RFID identifiers, beacon scanners to read beacon based identifiers, NFC readers to read NFC tags, and/or Bluetooth scanners to read Bluetooth identifiers).

Figure 1B:
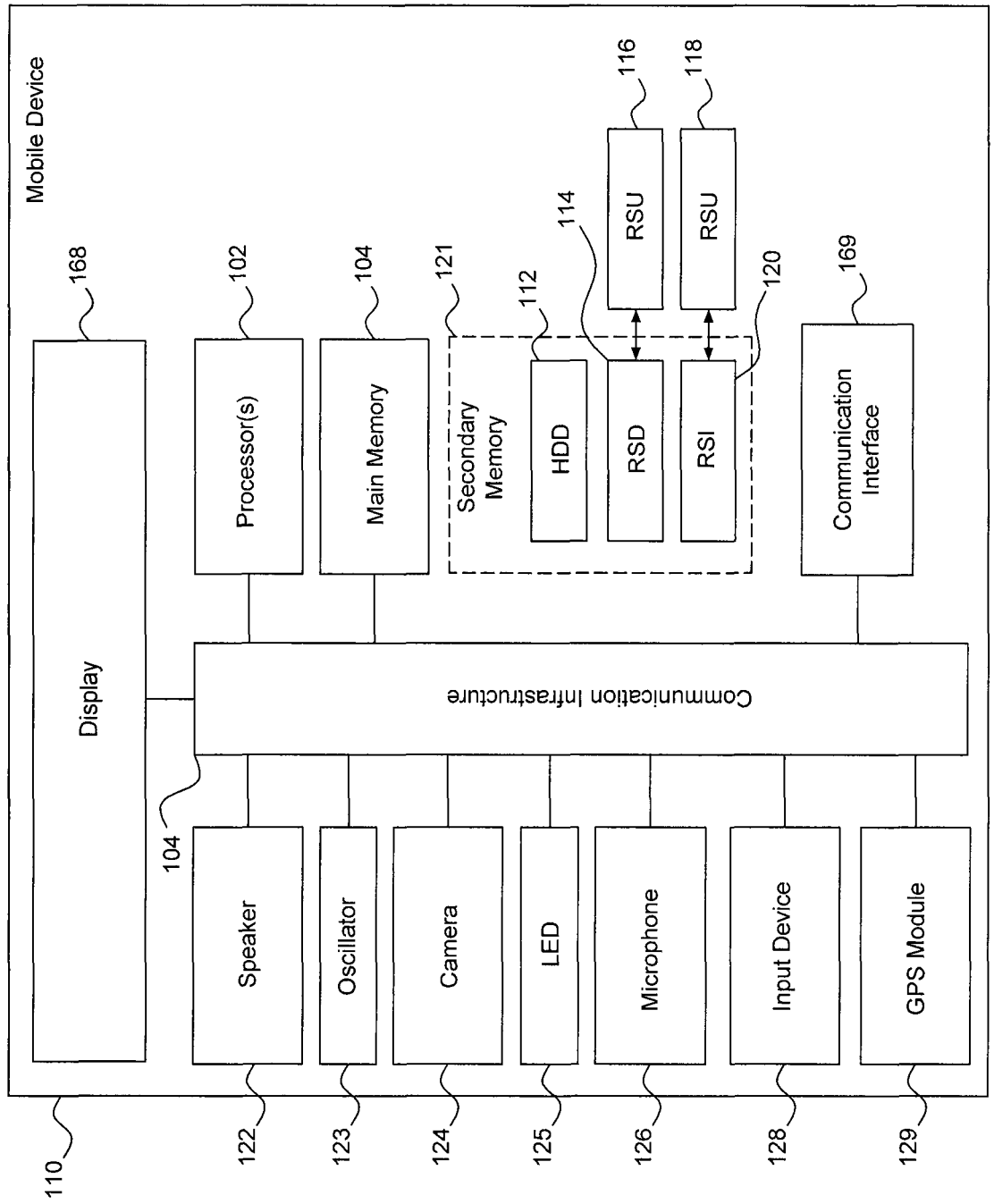
FIG. 1B illustrates one example of an architecture of a mobile device in accordance with some embodiments of the present disclosure.

FIG. 1B is a block diagram of one example of an architecture of client device 110. As shown in FIG. 1B, client device 110 includes one or more processors, such as processor(s) 102. Processor(s) 102 may be any central processing unit ("CPU"), microprocessor, micro-controller, or computational device or circuit for executing instructions. Processor(s) are connected to a communication infrastructure 104 (e.g., a communications bus, cross-over bar, or network). Various software embodiments are described in terms of this exemplary mobile device 110. After reading this description, it will be apparent to one of ordinary skill in the art how to implement the method using client devices 110 that include other systems or architectures. One of ordinary skill in the art will understand that computers 34, 54 may have a similar and/or identical architecture as that of client devices 110. Put another way, computers 34, 54 can include some, all, or additional functional components as those of the client device 110 illustrated in FIG. 1B.

Client device 110 includes a display 168 that displays graphics, video, text, and other data received from the communication infrastructure 104 (or from a frame buffer not shown) to a user (e.g., a subscriber, commercial user, back-end user, or other user). Examples of such displays 168 include, but are not limited to, LCD screens, OLED display, capacitive touch screen, and a plasma display, to list only a few possible displays. Client device 110 also includes a main memory 108, such as a random access ("RAM") memory, and may also include a secondary memory 110. Secondary memory 110 may include a more persistent memory such as, for example, a hard disk drive ("HDD") 112 and/or removable storage drive ("RSD") 114, representing a magnetic tape drive, an optical disk drive, solid state drive ("SSD"), or the like. In some embodiments, removable storage drive 114 reads from and/or writes to a removable storage unit ("RSU") 116 in a manner that is understood by one of ordinary skill in the art. Removable storage unit 116 represents a magnetic tape, optical disk, or the like, which may be read by and written to by removable storage drive 114. As will be understood by one of ordinary skill in the art, the removable storage unit 116 may include a tangible and non-transient machine readable storage medium having stored therein computer software and/or data.

In some embodiments, secondary memory 110 may include other devices for allowing computer programs or other instructions to be loaded into client device 110. Such devices may include, for example, a removable storage unit ("RSU") 118 and a corresponding interface ("RSI") 120. Examples of such units 118 and interfaces 120 may include a removable memory chip (such as an erasable programmable read only memory ("EPROM")), programmable read only memory ("PROM")), secure digital ("SD") card and associated socket, and other removable storage units 118 and interfaces 120, which allow software and data to be transferred from the removable storage unit 118 to client device 110.

Client device 110 may also include a speaker 122, an oscillator 123, a camera 124, a light emitting diode ("LED") 125, a microphone 126, an input device 128, and a global positioning system ("GPS") module 129. Examples of input device 128 include, but are not limited to, a keyboard, buttons, a trackball, or any other interface or device through a user may input data. In some embodiment, input device 128 and display 168 are integrated into the same device. For example, display 168 and input device 128 may be touch-screen through which a user uses a finger, pen, and/or stylus to input data into client device 110.

Client device 110 also includes one or more communication interfaces 169, which allows software and data to be transferred between client device 110 and external devices such as, for example, another client device 110, a computer 34, 54 and other devices that may be locally or remotely connected to mobile device 100. Examples of the one or more communication interfaces 169 may include, but are not limited to, a modem, a network interface (such as an Ethernet card or wireless card), a communications port, a Personal Computer Memory Card International Association ("PCMCIA") slot and card, one or more Personal Component Interconnect ("PCI") Express slot and cards, or any combination thereof. The one or more communication interfaces 169 may also include a wireless interface configured for short range communication, such as near field communication ("NFC"), Bluetooth, or other interface for communication via another wireless communication protocol. As briefly noted above, one of ordinary skill in the art will understand that computers 34, 54 and portions of system 100 may include some or all components of client device 110.

Software and data transferred via the one or more communications interfaces 169 are in the form of signals, which may be electronic, electromagnetic, optical, or other signals capable of being received by communications interfaces 169. These signals are provided to communications interface 169 via a communications path or channel. The channel may be implemented using wire or cable, fiber optics, a telephone line, a cellular link, a radio frequency ("RF") link, or other communication channels.

In this document, the terms "non-transitory computer program medium" and "non-transitory computer readable medium" refer to media such as removable storage units 116, 118, or a hard disk installed in hard disk drive 112. These computer program products provide software to client device 110. Computer programs (also referred to as "computer control logic") may be stored in main memory 108 and/or secondary memory 110. Computer programs may also be received via the one or more communications interfaces 169. Such computer programs, when executed by a processor(s) 102, enable the client device 110 to perform the features of the method discussed herein.

Figure 1C:
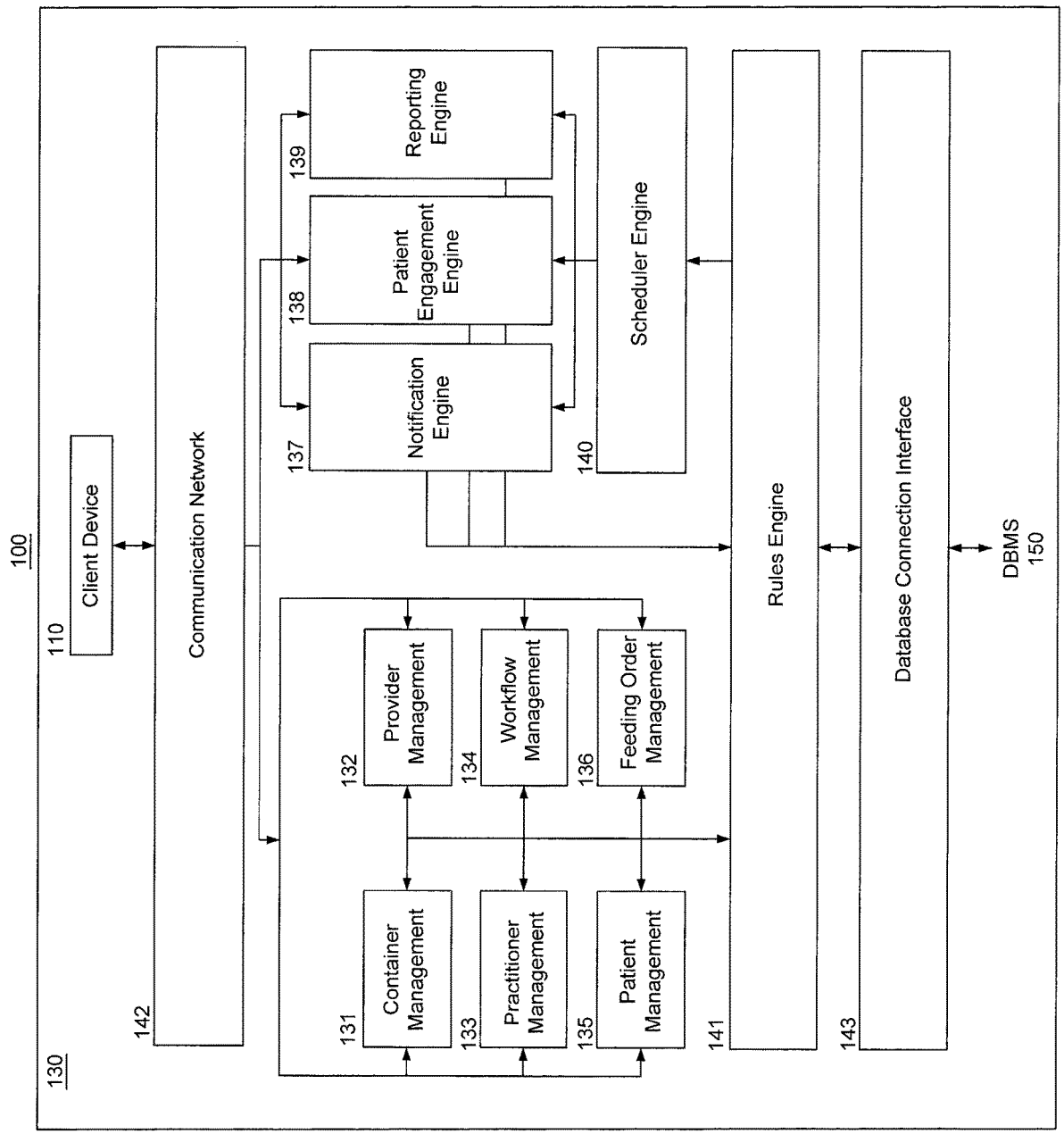
FIG. 1C is a diagram of system server components in accordance with some embodiments of the present disclosure.

FIG. 1C is a diagram of system 100 management server 130 components in accordance with some embodiments of the present disclosure. System 100 may be a computing environment including one or more client devices 110, management server 130, one or more software management modules 131, 132, 133, 134, 135, and 136, one or more software engines 137, 138, 139, 140, and 141, database connection interface 143, database management system 150, and a communication network 142 connecting various components of system 100. Although one client device 110 is shown in FIG. 1C, any number of client devices may be present. In various embodiments, client device 110 is a user device capable of connecting to the Internet or similar network as will be described below. In some embodiments, at least one device is a caretaker client device 110-1 and a patient (e.g., mother, parent, parental custodian, etc.) client device 110-2.

In various embodiments, as shown in FIG. 1C, management server 130 may comprise a rules engine 141 in communication with a database management system 150 via a database connection interface 143. In some embodiments, rules engine 141 is executed by a processor, which reads rules stored in database management system 150 and returns processed rules for use by management modules 131, 132, 133, 134, 135, and 136 and scheduler engine 140. As will be discussed in further detail below, for example, container management 131 is a module that reads rules from rules engine 141 and processes requests from client device 110 via communication network 142 for creating, reading, updating or deleting container identifier information. In this example, container management 131 returns the respective requested data regarding container management back to the client device 110, as will be discussed in more detail below.

Various components of the computing environment 100 are configured to address problems associated with milk management workflows (e.g., container identification, verification, and validation), notifications, patient engagement with lactation assistance, and tracking of analytical data concerning milk. Various components of computing environment 100 address these problems by providing automated milk management processes, secured media (e.g., images, videos, audio, etc.) communications, and analytical tracking tools.

The resulting processing architecture of system 100 facilitates milk management by permitting users to identify, verify, and validate milk containers according to container identifiers, bid identifiers, and patient identifiers. A container identifier is an identifier on a container to assign a milk container to a mother, source (e.g., for donor or formula milk) feeding order, or to a batch (e.g., for donor or formula milk), as will be discussed further below. In some embodiments, a bin identifier is an identifier on a bin to store containers of a mother, her infants (e.g., one or more), or store donor or formula feeds, and an infant identifier is an identifier in the unit to uniquely identify the infant from other infants. As will be described below an identifier may be located on a label of the container or bin and may comprise a 1D barcode identifier (e.g., code-128, code-39, etc.), 2D barcode identifier (e.g., QR codes, etc.), radio frequency identifiers (RFID), beacon based identifiers, NFC tags, Bluetooth identifiers, or any suitable identification means for assignment as would be understood by one of ordinary skill in the art.

System 100 maintains a database of container identifiers, bin identifiers, infant identifiers and various additional identification information that are used to aid in various workflows (e.g., actions, tasks, etc.) associated with breastmilk management described below. Computing environment 100 is further configured to improve patient engagement by providing comprehensive media (e.g., images, video, audio, etc.) sharing communications between a plurality of users on respective client devices 110.

In some embodiment, system 100 may comprise a printer (not shown) communicatively coupled to server 100 and/or client device 110. A printer may be any printing device that is used to generate container identifiers, bin identifiers, infant identifiers, or any other suitable label or marker for determining the characteristics of milk disposed within storage as described throughout this specification.

In various embodiments, as shown in FIG. 1A-1E, client device 110 may include a computing device such as a hashing computer, a personal computer, a laptop computer, a tablet computer, a notebook computer, a hand-held computer, a personal digital assistant, a portable navigation device, a mobile phone, a smart phone, a wearable computing device (e.g., a smart watch, a wearable activity monitor, wearable smart jewelry, and glasses and other optical devices that include optical head-mounted displays (OHMDs)), an embedded computing device (e.g., in communication with a smart textile or electronic fabric), or any other suitable computing device configured to store data and software instructions, execute software instructions to perform operations, and/or display information on a display device. Client device 110 may be associated with one or more users (not shown). For example, a user operates client device 110, causing it to perform one or more operations in accordance with various embodiments.

Client device 110 includes one or more tangible, non-transitory memories that store data and/or software instructions, and one or more processors configured to execute software instructions. Client device 110 may include one or more display devices that display information to a user and one or more input devices (e.g., keypad, keyboard, touch-screen, voice activated control technologies, or any other suitable type of known input device) to allow the user to input information to the client device. Client device 110 processor(s) may be any central processing unit ("CPU"), microprocessor, micro-controller, or computational device or circuit for executing instructions. Processor(s) are connected to a communication infrastructure (e.g., a communications bus, cross-over bar, or network). Various software embodiments are described in terms of this exemplary client device 110. After reading this description, it will be apparent to one of ordinary skill in the art how to implement the method using client device 110 that include other systems or architectures. One of ordinary skill in the art will understand that computers may have a similar and/or identical architecture as that of client device 110. Put another way, computers can include some, all, or additional functional components as those of the client device 110 illustrated in FIG. 1A-1E.

Client device 110 may also include a speaker, an oscillator, a camera, a light emitting diode ("LED"), a microphone, an input device, and a global positioning system ("GPS") module. Examples of input devices include, but are not limited to, a keyboard, buttons, a trackball, or any other interface or device through a user may input data. In some embodiment, input devices and display (e.g., user interface 168) are integrated into the same device. For example, user interface 168 and the input device may be touchscreen through which a user uses a finger, pen, and/or stylus to input data into client device 110.

Client device 110 also includes one or more communication interfaces, which allows software and data to be transferred between client device 110 and external devices such as, for example, another client device 110, a computer, management server 130, and other devices that may be locally or remotely connected to client device 110. Examples of the one or more communication interfaces may include, but are not limited to, a modem, a network interface (e.g., communication interface 169, such as an Ethernet card or wireless card), a communications port, a Personal Computer Memory Card International Association ("PCMCIA") slot and card, one or more Personal Component Interconnect ("PCI") Express slot and cards, or any combination thereof. The one or more communication interfaces may also include a wireless interface configured for short range communication, such as near field communication ("NFC"), Bluetooth, or other interface for communication via another wireless communication protocol.

Software and data transferred via the one or more communications interfaces 169 are in the form of signals, which may be electronic, electromagnetic, optical, or other signals capable of being received by communications interfaces. These signals are provided to communications interface 169 via a communications path or channel. The channel may be implemented using wire or cable, fiber optics, a telephone line, a cellular link, a radio frequency ("RF") link, or other communication channels.

In an embodiment where the system 100 or method is partially or entirely implemented using software, the software may be stored in a computer program product and loaded into client device 110 using removable storage drive, hard drive, and/or communications interface. The software, when executed by processor(s), causes the processor(s) to perform the functions of the method described herein. In another embodiment, the method is implemented primarily in hardware using, for example, hardware components such as application specific integrated circuits ("ASICs"). Implementation of the hardware state machine so as to perform the functions described herein will be understood by persons skilled in the art. In yet another embodiment, the method is implemented using a combination of both hardware and software.

Embodiments of the subject matter described in this specification can be implemented in a system 100 that includes a back end component, e.g., as a data server, or that includes a middleware component, e.g., an application server, or that includes a front end component (e.g., a client device 110) having a graphical user interface or a Web browser through which a user can interact with an implementation of the subject matter described is this specification, or any combination of one or more such back end, middleware, or front end components. The components of the system can be interconnected by any form or medium of digital data communication, (e.g., a communication network 142). Communications network 142 may include one or more communication networks or media of digital data communication. Examples of communication network 142 include a local area network ("LAN"), a wireless LAN, a RF network, a Near Field Communication (NFC) network, (e.g., a "WiFi" network), a wireless Metropolitan Area Network (MAN) connecting multiple wireless LANs, NFC communication link(s), and a wide area network ("WAN"), e.g., the Internet and combinations thereof. In accordance with various embodiments of the present disclosure, communications network 142 may include the Internet and any publicly accessible network or networks interconnected via one or more communication protocols, including, but not limited to, hypertext transfer protocol (HTTP) and HyperText Transfer Protocol Secured (HTTPS) and Secured Socket Layer/Transport Layer Security (SSL/TLS) and transmission control protocol/internet protocol (TCP/IP). Communications protocols in accordance with various embodiments also include protocols facilitating data transfer using radio frequency identification (RFID) communications and/or NFC. Moreover, communications network 142 may also include one or more mobile device networks, such as a GSM or LTE network or a PCS network, allowing a client device to send and receive data via applicable communications protocols, including those described herein. For ease of illustration, communication network 142 is shown as an extension of management server 130.

A client device 110 and server 130 are generally remote from each other and typically interact through a communication network 142. The relationship of client device 110 and management server 130 arises by virtue of computer programs running on the respective system components and having a client-server relationship to each other. System 100 may include a web/application server (not shown) in embodiments used to gain access to many services provided by management server 130.

Figure 1D:
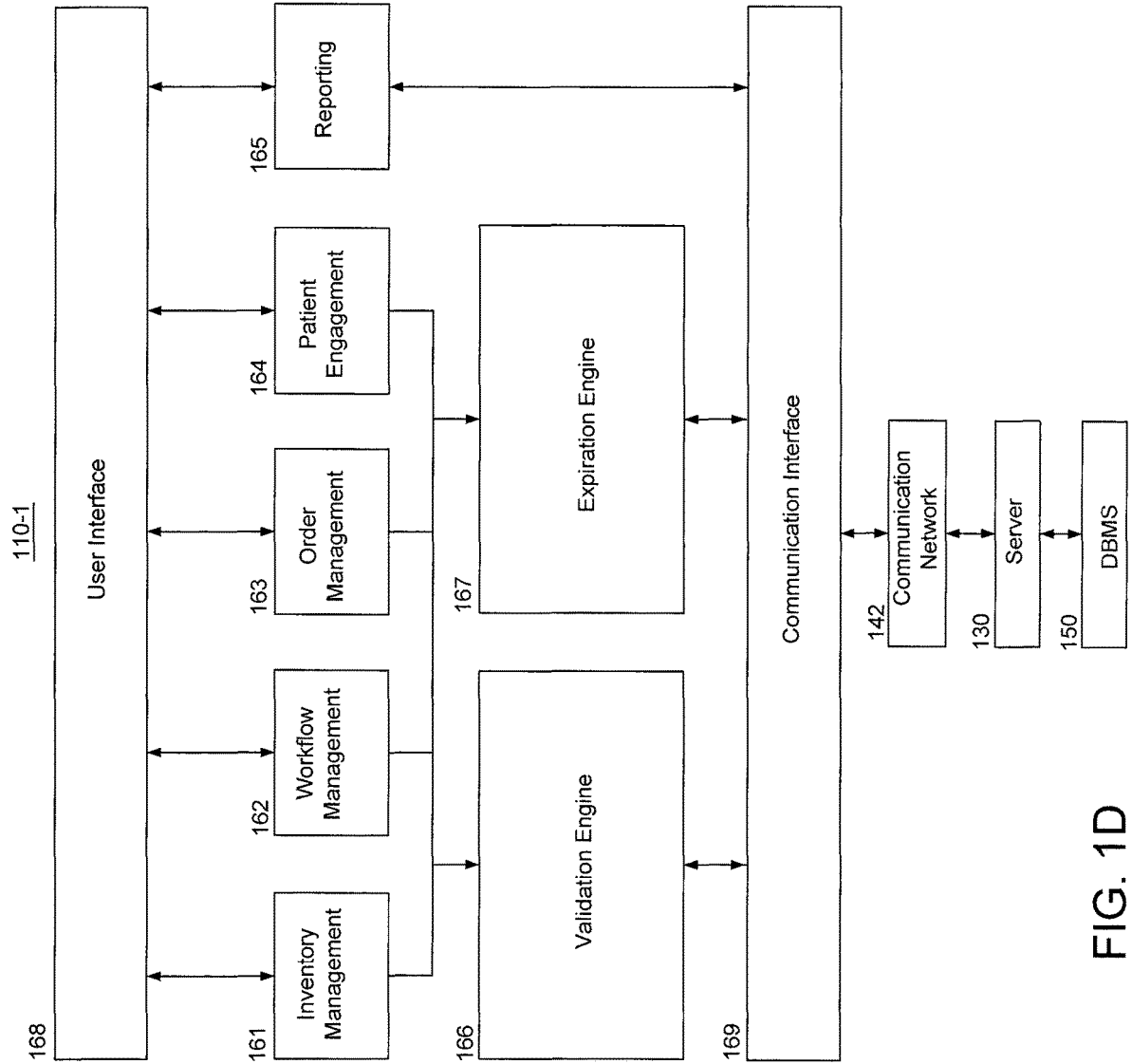
FIG. 1D is a diagram of caretaker client device application components in accordance with some embodiments of the present disclosure.

FIG. 1D is a diagram of caretaker client device 110-1 application components in accordance with some embodiments of the present disclosure. In one aspect, client device 110 stores in memory one or more software applications that run on the client device and are executed by the one or more processors. In some instances, each client device stores software applications that, when executed by one or more processors, perform operations that establish communications with management server 130 (e.g., across communication network 142 via communication interface 169) and that obtain, from management server 130, information or data via database management system 150 in accordance with various embodiments.

Referring to FIG. 1D, caretaker client device 110-1 application components may be a computing environment including one or more processing modules 161, 162, 163, 164, and 165, one or more engines 166 and 167, communication interface 169, and user interface 168. According to various embodiments, one or more processing modules 161, 162, 163, 164, and 165, process user input via user interface 168 for various functions, workflows, and tasks on client device 110. For example, inventory management module 161 is a module that includes instructions for processing user input for any inventory related tasks (e.g., show inventory, container transfer, emptying a container, receiving a container, discharging a container, etc.). In this example, inventory management 161 updates the user interface 168 with processed data. Concurrently, one or more processing modules 161, 162, 163, 164, and 165, may interact with one or more engines 166 and 167. For example, inventory management module 161 may interact with validation engine 166 to ensure the validity of data that is being processed by the processing modules and being returned from management server 130, according to various embodiments discussed in further detail below.

Figure 1E:
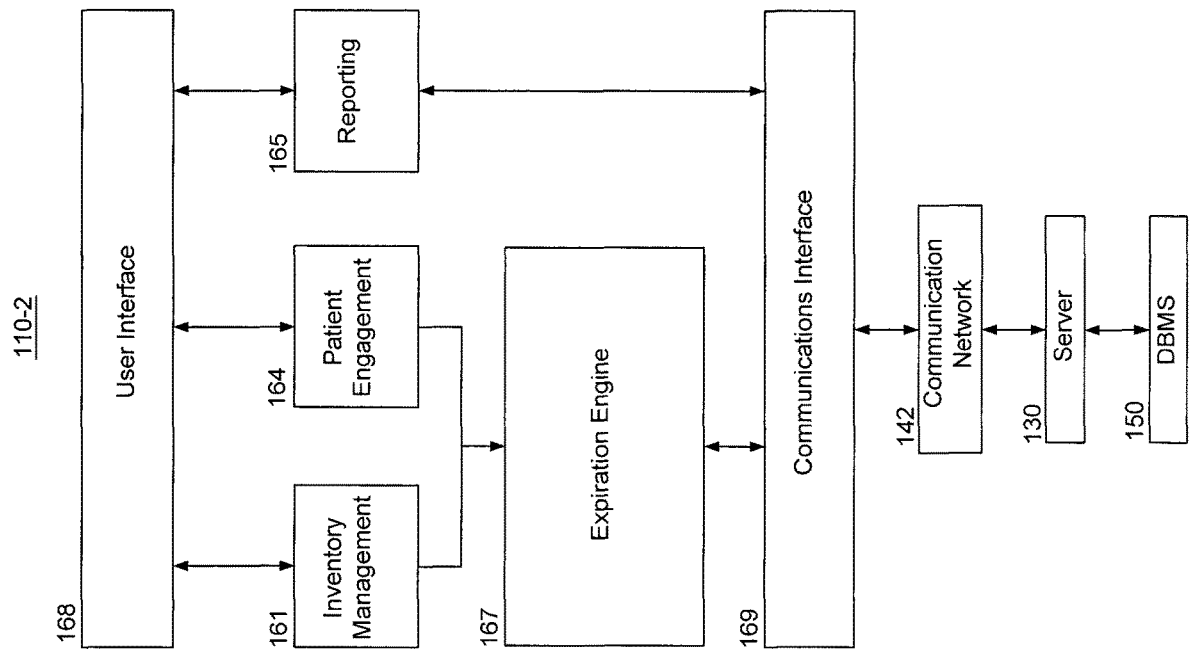
FIG. 1E is a diagram of patient client device application components in accordance with some embodiments of the present disclosure.

FIG. 1E is a diagram of system patient (e.g., mother, parent, parental custodian, etc.) client device 110-2 application components in accordance with some embodiments of the present disclosure. Patient (e.g., mother, parent, parental custodian, etc.) client device 110-2 application components may include one or more processing modules 161, 164, and 165, one or more engines 167, communication interface 169, and user interface 168. One or more processing modules 161, 164, and 165, process user input via user interface 168 for various functions, workflows, and tasks on client device 110. As will be disclosed in further detail below, for example, reporting module 165 processes user input for any patient engagement related tasks (e.g., displays daily statistics, displays mother's pumping pattern dashboards, etc.). As will be described in further detail below, the one or more engines may include an expiration engine 167 that identifies respective rules from management server 130 via rules engine 141 of management server 130, for updating the expiration date/time of a container based on the identified respective rules.

In various embodiments, client device 110 may execute the stored software application(s) to interact with management server 130 via a network connection. The executed software applications may cause client device 110 to communicate information (e.g., milk management identification information, patient engagement information, lactation analytics, etc.). As described below, executed software application(s) may be configured to allow a user associated with client device 110 to identify one or more containers using an imaging device (e.g., a still or video camera or similar device that can image an identifier) or other identification means to track, verify, and validate milk information disposed within the container or bin. In some embodiments, identification of a container means using a device to read the container, bin, or infant identifier. Stored software application(s) on client device 110 are configured to access webpages on the Internet or other suitable network based communication capable of interacting with communication network 142, as would be understood by one of ordinary skill in the art. For example, a user may access a user account on management server 130 via an Internet webpage. In this example, management server 130 is configured to render the Internet webpage for the user on client device 110. Alternatively, management server 130 may provide information to stored software application(s) on client device 110 via communication network 142. In this example, client device 110 will display information provided by management server 130 using a stored software application(s) graphical user interface display.

According to various embodiments, system 100 includes database management system/storage 150 for managing and storing data, such as container identifiers and other data maintained by the management server 130. The database management system and/or storage are referred to herein simply as DBMS 150 for convenience. DBMS 150 is communicatively coupled with various modules and engines as illustrated in FIG. 1A-1E and FIG. 2A.

It should be understood that various forms of data storage or repositories can be used in system 100 that may be accessed by a computing system, such as hard drives, tape drives, flash memory, random-access memory, read-only memory, EEPROM storage, in-memory databases like SAP HANA, and so on, as well as any combination thereof. Stored data may be formatted within data stores in one or more formats, such as flat text file storage, relational databases, non-relational databases, XML, comma-separated values, Microsoft Excel files, or any other format known to those of ordinary skill in the art, as well as any combination thereof as is appropriate for the particular use. Data stores may provide various forms of access to the stored data, such as by file system access, network access, a SQL protocol (e.g. ODBC), HTTP, FTP, NES, CIFS, and so on, as well as any combination thereof.

Figure 2A:
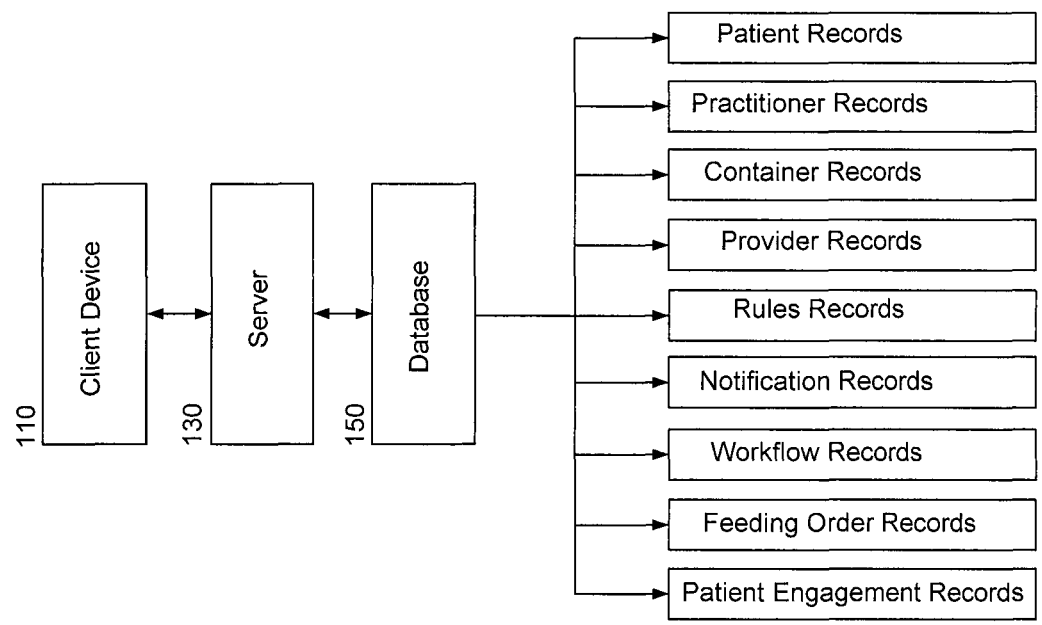
FIG. 2A is a diagram of system components for database design in accordance with some embodiments of the present disclosure.

FIG. 2A is a diagram of system components for database design in accordance with some embodiments of the present disclosure, and FIG. 2B depicts an example database schema for the management of milk containers in accordance with some embodiments of the present disclosure. As shown in FIG. 2A, client device 110 is configured to access DBMS 150 via management server 130. In various embodiments, DMBS 150 is configured to maintain a database schema 180. FIG. 2A shows an exemplary database schema 180. FIG. 2B shows exemplary identifiers associated with the categories of database schema 180. As will be described in further detail below, database schema 180 is configured to maintain a plurality of identifiers associated with specific categories of records. For example, database schema 180 may be arranged to maintain identifiers in columns within DBMS 150 associated with container records, patient records, practitioner records, workflow records, nutrition/feeding order records, notification records, rule records, provider records, and patient engagement records. In this aspect, identifiers refer to specific information pertaining to the categories described above. For example, the container category may include identifiers concerning the expiration date and/or side of the breast that provided the milk. Database schema 180 within DMBS 150 may be arranged or organized in any suitable manner within the milk management system. Although FIG. 2B identifies categorical identifiers as described above, any number of suitable identifiers may be used to maintain records associated with the system described herein. In addition, database schema 180 may contain additional categories and identifiers not depicted in FIG. 2A and FIG. 2B for maintaining record data in system 100.

The database schema of FIG. 2B advantageously organizes identifiers in a way that permits the system to operate more efficiently. In some embodiments, categories of identifiers in database schema FIG. 2B, increase efficiency by grouping identifiers with an associated management model of management server 130.

In various embodiments, management server 130 includes computing components configured to store, maintain, and generate data and software instructions. For example, management server 130 may include or have access to one or more processors 24, one or more servers (not shown) and tangible, non-transitory memory devices (e.g., local data store (in addition to DBMS 150)) for storing software or code for execution and/or additional data stores. Servers may include one or more computing devices configured to execute software instructions stored on to perform one or more processes in accordance with various embodiments. In some embodiments, DBMS 150 includes a server that executes software instructions to perform operations that provide information to at least one other component of computing environment 100, for example providing data to another data store or to third party recipients (e.g., unit, hospital, milk storage facility, etc.) through a network, such as communication network 142.

Management server 130 may be configured to provide one or more websites, digital portals, or any other suitable service that is configured to perform various functions of management server 130 components. In some embodiments, management server 130 maintains application programming interfaces (APIs) through which the functionality and services provided by server 130 may be accessed through one or more application programs executed by a client device 110. Exemplary services and systems provided by management server 130 include container management 131, provider management 132, practitioner management 133, workflow management 134, patient management 135, and feeding order management 136, each of which is described in further detail below. In various embodiments, management server 130 may provide information to software application(s) on client device 110 for display on a graphical user interface 168.

In some embodiments, management server 130 provides information to client device 110 (e.g., through the API associated with the executed application program). Client device 110 presents portions of the information to corresponding users through a corresponding respective graphical user interface 168 or webpage.

In various embodiments, management server 130 is configured to provide or receive information associated with services provided by management server 130 to client device 110. For example, client device 110 may receive information via communication network 142, and store portions of the information in a locally accessible store device and/or network-accessible storage devices and data stores (e.g., cloud-based storage). For example, client device 110 executes stored instructions (e.g., an application program, a web browser, and/or a mobile application) to process portions of stored data and render portions of the stored data for presentation to the respective user or users. Management server 130 may include additional servers (not shown) which may be incorporated as a corresponding node in a distributed network or as a corresponding networked server in a cloud-computing environment. Furthermore, servers may communicate via communication network 142 with one or more additional servers (not shown), that may facilitate the distribution of processes for parallel execution by the additional servers.

In further aspects, management server 130 may represent a "controlling entity" capable of storing, managing, distributing, and safeguarding information (e.g., container identification, patient information, practitioner information, and/or rules for milk management, etc.) in accordance with various embodiments.

The present disclosure describes systems and methods that provide for an automated milk management solution to streamline workflow management throughout container lifecycles utilizing an organizational solution for maintaining identifiers associated with all aspects of the container. Additionally, the system and methods described herein solve conventional patient engagement issues by providing a media-sharing platform, a notification platform, and a chat platform (text/audio/video chat or call), that provide intrinsic motherhood benefits by naturalizing the usage of a breast pump, with the goal of improving lactation and addressing issues concerning lactation. Conventional tracking and analytics problems are addressed in the present disclosure by providing systems and methods for container management with respect to expiration and inventory. Finally, comprehensive notification and real-time dashboard are provided to users to proactively address supply and pumping pattern issues. As will be further described below with reference to FIG. 1A-1E, the system described herein includes a milk management system configured to streamline workflow steps using automated identification, verification, validation and information exchange processes, as described throughout this specification.

Workflow Management

Figure 3:
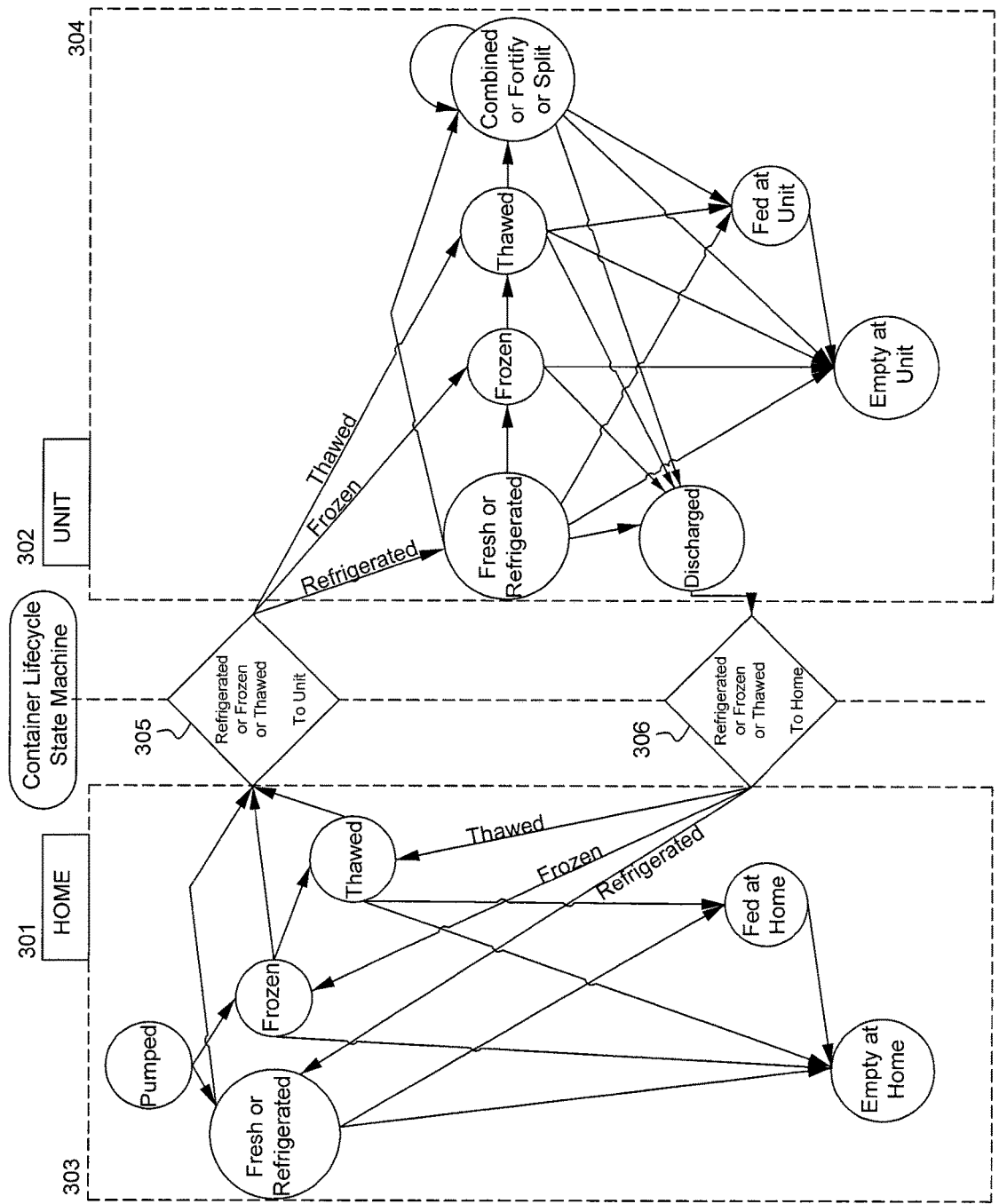
FIG. 3 is a state diagram illustrating example milk container states in accordance with some embodiments of the present disclosure.

FIG. 3 is a state diagram illustrating example breast milk container states in accordance with some embodiments of the present disclosure. The example state diagram of FIG. 3 illustrates example workflows that or states that a milk container may experience. FIG. 3 is divided into two sections (e.g., locations), home 301 and unit 302, for any given container state group, home state group 303 and unit state group 304. Unit 302, as referred to throughout this disclosure, may be any neonatal intensive care unit (NICU), pediatric intensive care unit (PICU), intensive care nursery (ICN), maternity ward, post-partum care unit, pediatric unit, day care center, school, or any other suitable setting where an infant might be fed milk. A location describes where the container exists at any given container state. Although, two locations are shown, a container state may exist in a location not shown, but managed using the systems and methods described herein. A container state refers to the physical action associated with the milk disposed within a container. For example, when a mother pumps breast milk for a child, the container may be generated at home 301 In this example, the state of the breast milk is "pumped" as shown in FIG. 3 in the home state group 303. FIG. 3 shows the possible state changes (e.g., physical actions associated with the state of a container) and/or the milk disposed within a container. Using the example above, when a mother pumps breast milk for storage, the pumped state first occurs in the home 301 location of the container lifecycle. The milk once in a pumped state may be transferred to storage in a fresh/refrigerated state or a frozen state. If the milk is discarded from a frozen state it transitions to an empty at home state as depicted in FIG. 3. If the milk is thawed it transitions from a frozen state to a thawed state.

In reference to FIG. 3 and the examples above, state transitions may occur at 305 and 306. Specifically, at 305, milk in a refrigerated, thawed, or frozen state may be transferred to unit 302 via state transition 305. A state transition refers to a change in the location of the container. When containers are transferred from the home to the unit, a state transition occurs at 305 showing a transfer in location of the container. When containers are transferred from the unit to the home, a state transition occurs at 306 showing a transfer in location of the container. After state transition 305, the milk may be refrigerated, thawed, or frozen as shown in the unit state group 304. In some embodiments, milk in a refrigerated state may undergo a fortification process at the fortification state in unit state group 304. Fortification, as referred to throughout this disclosure, is the process of strengthening breast milk with fortifiers (e.g., Vitamin A, Vitamin D, etc.) before infant consumption. In this embodiment, milk transitions from a fresh or refrigerated state to a fortified state. In some embodiments, milk may be combined or split after a fresh or refrigerated state. For example, once a container is split, it may be combined/split/fortified, transition to a discharged, empty at unit, or fed at unit state 304. In various embodiments, as shown in FIG. 3, a container may split and/or fortified, as shown in the self-reference arrow at unit state 304. For example, once a container is split, it may transition to a discharged, empty at unit, or fed at unit state 304. In some aspects, as show in FIG. 3, a container may transition from a discharged state at the unit 302 back to the home 301 in a fresh or refrigerated, frozen, or thawed state via a state transition 306. Additional state diagrams may exist for donor milk and formula milk that comprise the same or different container states from those identified in FIG. 3.

In various embodiments, system 100 is configured to address a variety of workflow problems that exist with conventional milk management methods. A workflow as described throughout this specification refers to a state change or state transition as described above. In some embodiments, milk management workflows include state changes or state transitions that occur during container inventory maintenance processes (e.g., receiving, discharging, etc.), container verification, and validation (e.g., mother to infant mapping). In some embodiments, a workflow may include when the container is fortified. In various embodiments, a workflow may include when a container is delivered for feeding. A workflow may include any step/action associated with a state change, state transition, or other action that may occur with a container and/or performed on milk disposed within a container as would be understood by one of ordinary skill in the art.

Examples of a conventional workflow problem with milk management include the mothers use of a breast pump to express milk into containers provided by the unit. The number of containers possessing breast milk that the mother delivers to the unit may be between 12 to 16 containers for a given day, as described above. For each container, the mother must manually write the date and timestamp of pumping on each label affixed to the container. In this example, the mother brings the breast milk filled containers into the unit, where each container label is checked by a caretaker. The caretaker then scans the label and manually creates the same date and time stamps as recorded by the mother, and enters this information into a database. Any state change or action (e.g., receiving, discharging, feeding, fortifying, splitting, combining, etc.) on a container or containers requires a manual two caretaker check/verification to ensure the correctness of the container.

The correctness of the container refers to rules for determining the management of the container. For example, a rule may include that a container is set to expire at a specified time after being stored in a refrigerator for a specified date and time. In some embodiments, a rule may include that the container is correctly associated with the intended mother. In various embodiments, a rule may include that a container should not be thawed if it is being frozen. Conventional methods of verifying rule correctness required a caretaker to verify manually in the database that the container satisfied all of the rule requirements before making a state change or state transition on a container.

Figure 4:
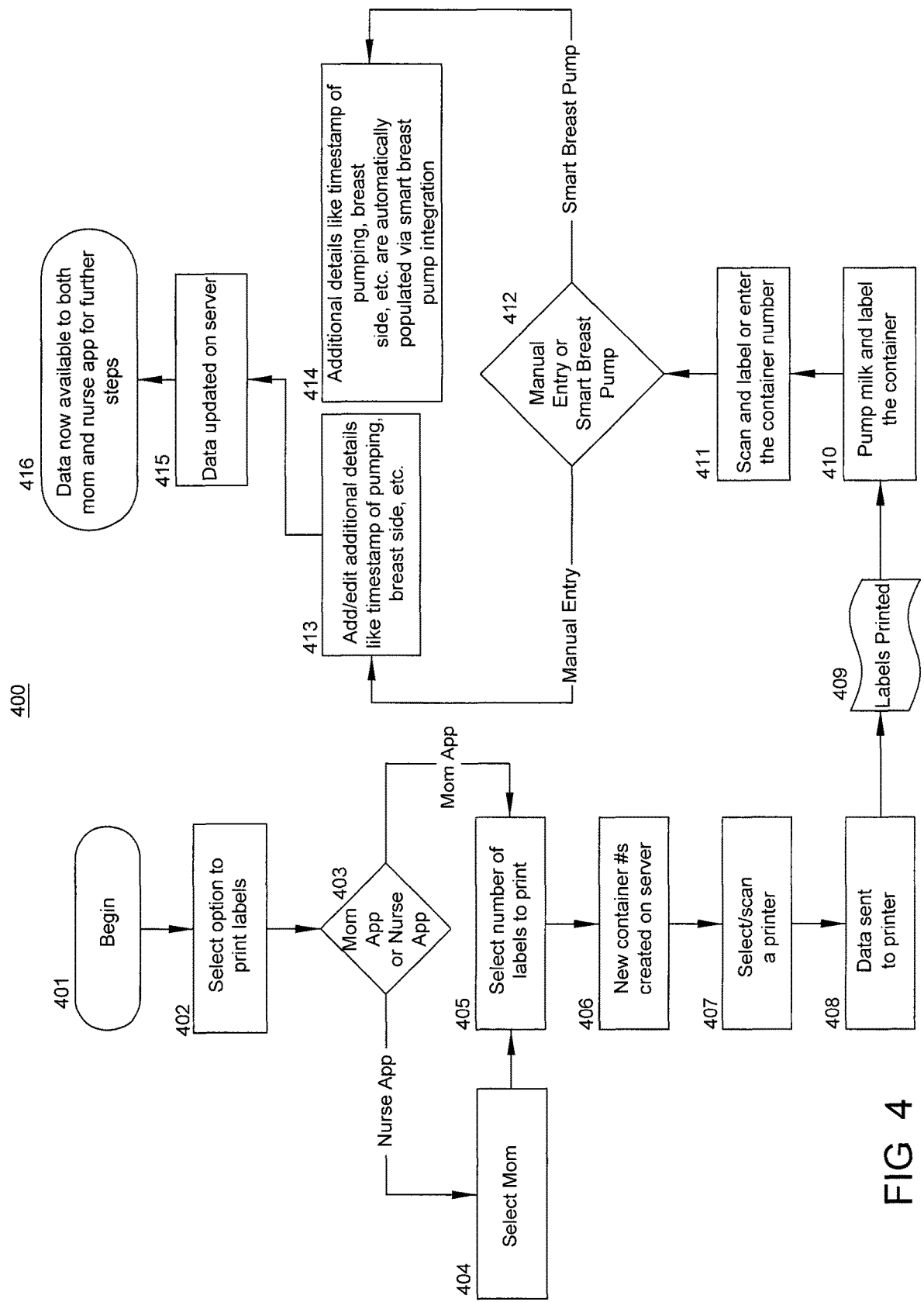
FIG. 4 is a flow diagram illustrating an example end-to-end automation process in accordance with some embodiments of the present disclosure.

FIG. 4 is a flow diagram illustrating an example end-to-end automation process 400 in accordance with some embodiments of the present disclosure. System 100 is configured to provide end-to-end automation of container management by providing pre-printed labels with container identifiers associated with identity/identifier information of the milk. FIG. 4 shows an example process 400 for end-to-end automation using pre-printed labels. The end-to-end automation process begins at 401.

At 402, a caretaker (e.g., nurse, technician, or other practitioner) or a mother may select an option to print labels associated with a container using client devices 110. This occurs by selecting an option using the display on client device 110 for printing labels on a printer communicably coupled to client device 110.

At 403, a caretaker may select to print labels using the caretaker client device 110-1 application identified in FIG. 1D, or a mother may select to print labels using the patient (e.g., mother, parent, parental custodian, etc.) client device 110-2 application identified in FIG. 1E, In various embodiments, labels may be printed using a printer communicably coupled to client device 110. In some embodiments, a user may select an option to print labels using display 168 on client device 110. In various embodiments, a client device application comprises features for printing labels via communication interface 169.

In the event that a caretaker is generating labels for a milk container, the caretaker selects the respective mother associated with the milk in the container at 404. In some embodiments, a respective mother may be selected using the display 168 of client device 110 via a client device application. In various embodiments, a caretaker may select a mother from a plurality of mothers assigned to a unit using client device 110 via a client device application.

At 405, the number of labels to print is selected.

At 406, container numbers are created by management server 130 and entered into DBMS 150 via the container management 131 module. For example, in some embodiments, the container management 131 module of server 130 reads rules from rules engine 141 and processes one or more user requests for creating, reading, updating, or deleting container records and returns identity information (e.g, milk and container identifier information).

At 407 and 408, a printer is selected or printer details are scanned or printer details are entered and the container identifier information is sent to the printer.

At 409, the container label is printed with the respective milk and container identifier information (e.g., identifiers). For example, a label may include mother identity information, hospital identifier, baby's identity information, baby's hospital identifier, container identity information (e.g., number, source, batch, or bin information), container identification (e.g., barcode, RFID, QR Code, NFC tag, etc.), etc. The label may include any identifier to describe information associated with the milk and/or the container.

In FIG. 4, milk is pumped or deposited (e.g., donor milk or formula milk) into the container and the printed label is affixed to the container at 410. At 411, the labeled container is scanned or the container number is manually entered into the computing environment 100 via client device 110. Client device 110 may use an imaging device to read a container identification visually, use an RFID scanner, NFC reader, beacon scanner, Bluetooth scanner, or any device for scanning, interrogating, or otherwise obtaining identifying information from a container as will be understood by one of ordinary skill in the art.

If at decision block 412, additional data is manually entered, a user either on the caretaker client device or the mother client device 110-2 may add or edit additional identifiers concerning the milk or container identifier information, at 413. For example, a user may update identifiers associated with the timestamp of when the milk was pumped or what side of the breast the milk was pumped from.

In some embodiments, system 100 is configured to capture data via client application generated from a smart breast pump. A smart breast pump is any breast pump capable of communicating information concerning the use of the breast pump. In some embodiments, system 100 is configured to be communicably coupled to a smart breast pump via a client device. In various embodiments, system 100 may accept data communication from a smart breast pump via a client device. If at decision block 412, a smart breast pump communicates additional identifiers (e.g., timestamp of pumping, breast side, etc.), the additional identifiers are automatically communicated and stored with the milk and container identifier information in DBMS 150, at 414.

The milk and container identifier information and additional user inputted identifiers are stored in DBMS 150 via management server 130 at step 415.

At 416, milk and container identifier information is available to the mother, caretaker, or any other individual with access to patient records.

As described above, any workflow (e.g., step or action) such as receiving, discharging, feeding, fortifying, splitting, combining for example, requires a manual 2-caretaker check/verification to ensure correctness of container(s). As described previously, correctness of the container refers to rules for determining the management of the container. The rules engine is configured to read rules from the database and return processed rules for use by other modules. A list of example rules concerning milk container management may include, but not be limited to, the following:

R1. Container expiration time based on R hours in refrigerator, F hours in freezer, T hours after thawing, O hours after fortifying, etc.;
R2. Container has not expired;
R3. Container is from the intended mother;
R4. Container is for the intended infant;
R5. Container has the correct fortification;
R6. Container is not to be thawed if it is being frozen;
R7. Container is not to be fortified it is being frozen;
R8. Container is not fortified if it is being fortified;
R9. Containers should not have different fortifications if they are being combined;
R10. When Combining, target container (can be a new or existing container) should get the same properties as the source containers. For example:
   Container A and Container B combine into container C;
   If Container A is thawed, then Container C should be marked as thawed; and/or
   If Container A is thawed, and Container B is colostrum, then Container C should be marked as "thawed+colostrum";
R11. When Splitting, target containers gets the same property as source container. For example:
   Container A is split into Container B and Container C;
   If Container A is fortified, then Container B and Container C should be marked as "fortified";
   If Container A is thawed, then Container B and Container C should be marked as "thawed";
   If Container A is colostrum, then container B and Container C should be marked as "colostrum"; and/or
   If Container A is fortified+thawed+colostrum (or any combination thereof), then Container B and Container C is marked as "fortified+thawed+colostrum" (or any combination thereof).

The above example rules may include fewer or additional rules not listed for the management of milk containers as would be understood by one of ordinary skill in the art. Additionally, the management of milk containers may contain one or more rules as described above for assisting caretakers with workflow processes.

In various embodiments, caretaker client device 110-1 of system 100, as shown in FIG. 1D, includes validation engine 166 configured to remove the need for a manual 2-caretaker check/verification. Validation engine 166 reads the applicable container rule(s) from rules engine 141 via DMBS 150 and processes the requisite rule(s) to ensure that data inputted pertaining to a container is validated against the applicable rule(s). For example, in a single workflow step (e.g., feeding, splitting, combining, etc.) multiple validations may be run, such as, checking that the bottle is from the correct mother, ensuring the bottle has not expired, verifying that the bottle has the correct fortification, etc. Each of these validations corresponds to a rule stored in the database and accessed via rules engine 141. System 100 is configured to remove the need for manual 2-caretaker check/verification by ensuring that all the required rule(s) conditions are met for different activities via validation engine 166. Rule(s) may be optionally configurable per the need of the unit (e.g., setting an expiry time for milk in the freezer).

Figure 5:
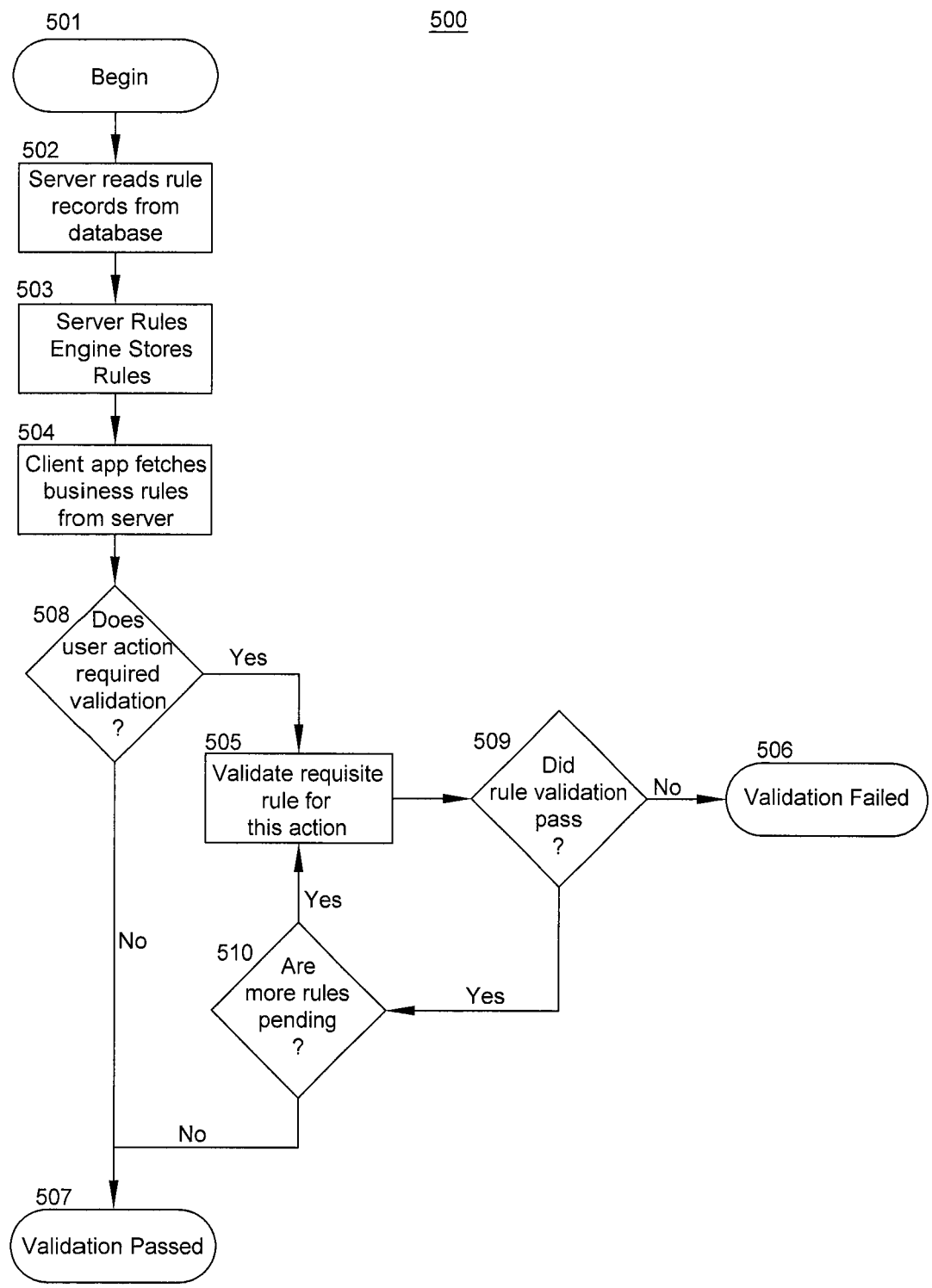
FIG. 5 is a flow diagram illustrating an example validation engine process in accordance with some embodiments of the present disclosure.

FIG. 5 is a flow diagram illustrating an example validation engine process 500 in accordance with some embodiments of the present disclosure. As described above, validation engine 166 reside within caretaker client device 110-1; however, one of ordinary skill in the art will understand that validation engine 166 could reside within another device of system 100, such as within management server 130, for example. Further, as noted above, validation engine 166 is configured to validate the data being provided to DBMS 150 and server 130 from caretaker client device 110-1. As described throughout this application, validating data means verifying that a rule permits the requested workflow. For example, a rule may be that the mother and the milk disposed within a container match. In this example, validation engine 166 will validate that the requested workflow (e.g., action) is permitted in view of the respective rule(s).

At 501, the validation engine process 500 begins.

At 502, management server 130 reads rules from DBMS 150 via rules engine 141 and database connection interface 143.

At 503, rules engine 141 of management server 130 stores rules retrieved from DBMS 150 for processing by at least one of the management modules 131, 132, 133, 134, 135, and/or 136.

As described above, in various embodiments, management server 130 includes management modules 131, 132, 133, 134, 135, and/or 136 to perform the functions of creating, reading, updating, or deleting container identifiers associated with a respective category of workflow processes, as will be discussed in more detail below. Based on the rules fetched from the database, each input sent to a management module is passed through the validation engine to ensure that appropriate rules for that management module are executed.

At 504, the caretaker client device 110-1 application retrieves rule(s) from management server 130 based on the respective workflow (e.g., action) requested by the client device.

At decision block 508, assuming that the rule(s) require validation, validation engine 166 validates the rule for the action that is being requested, at 505, on the caretaker client device 110-1 application. For example, if a caretaker is performing a feeding workflow process (e.g., action), the associated rule (e.g., or business rule if specific to the unit) may be that the container milk matches the milk the mother provided. In this example, validation engine 166 receives the scan information of the container and the mother, and then validates that information with the rule associated with the feeding workflow. In some embodiments, a specific workflow does not require validation. In that instance, validation engine 166 will return a passed or approved value to the caretaker client device 110-1 application indicating a successful validation.

In various embodiments, validation engine 166 may run one or more times, at 505, for each applicable rule as determined by rules stored in DBMS 150 and processed by rules engine 141.

At decision block 509, if the rule did not pass validation, at 506, validation engine 166 returns a failed or disapproved value to the caretaker client device 110-1 application indicating that the requested action has violated a rule and is subsequently disallowed. At decision block 510, if there are no pending rules to validate, the validation ends at 507. Using the above feeding example, if the container incorrectly matches the mother, validation engine 166 will return a failed or disapproved value to the caretaker client device 110-1 application. Assuming that all rules have been processed by validation engine 166 and are passed or approved, validation engine 166 will indicate to the caretaker client device 110-1 application that the requested action is approved (e.g., checked/verified) and may be performed. In various embodiments, the requested action is performed on client device 110. In some embodiments, a message is displayed on display 168 of client device 110 (or audio alert played) when the requested action is not valid.

In various embodiments, as described above, system 100 is configured to read container identifiers and store container identifiers automatically using an imaging or scanning device. In some embodiments, the mother client device 110-2 application may read container identifiers and store container identifiers in DBMS 150 via management server 130 for use at the unit. In this embodiment, when containers from the mother are received at the unit, the caregiver only needs to read the containers into the system and does not need to enter container identifiers manually. In some embodiments, the caregiver may input container identifier information manually. However, the automatic entry of container identifiers by the mother to be used by the caregiver is a tremendous time-saving expenditure that leads to increased productivity at the unit.

Figure 6:
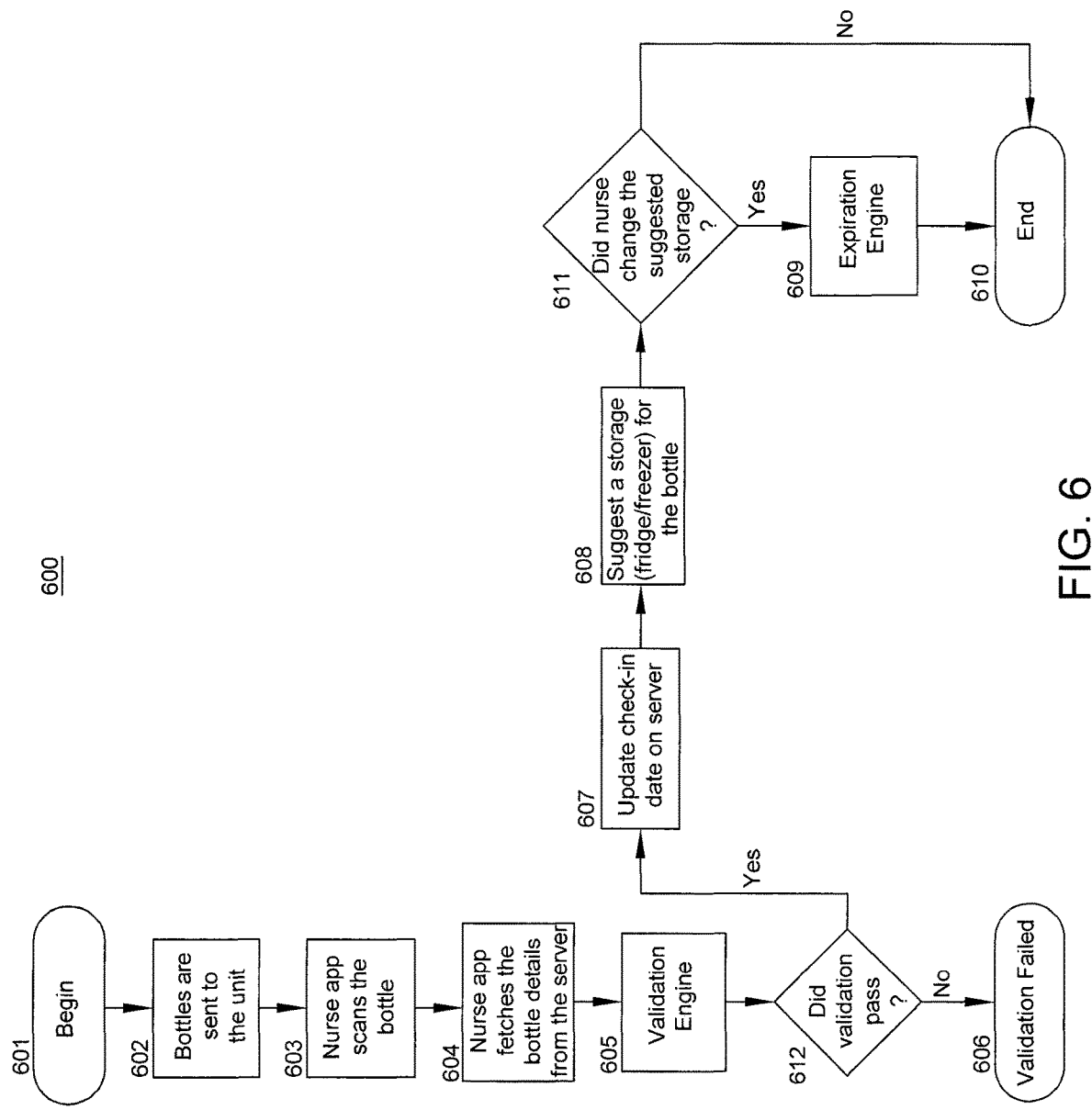
FIG. 6 is flow diagram illustrating an example receive workflow process in accordance with some embodiments of the present disclosure.

FIG. 6 is flow diagram illustrating an example receive workflow process 600 in accordance with some embodiments of the present disclosure. At 601, the receive workflow process 600 begins.

At 602, containers are sent to the unit (e.g., setting where an infant might be fed milk). As described above, the unit can include, but not be limited to, a NICU, postpartum hospital, milk donor bank, child day care, or other infant car unit.

At 603, a caretaker scans the container using a caretaker client device 110-1 or other device that is communicatively coupled to caretaker client device 110-1. In response to the scanning or interrogation of the container, the caretaker client device 110-1 receives identification information from the container.

At 604, when the container is scanned or manually entered, the caretaker client device 110-1 requests the management server 130 to retrieve container identifier information from DBMS 130 via database connection interface 143. In a receive workflow process 600, management server 130 processes the container via container management module 131. Container management module 131 reads rules from rules engine 141, and processes the request from caretaker client device 110-1 for creating reading, updating, and/or deleting container records and returns data information associated with the request.

In some embodiments, a workflow process may use one or more management modules 131, 132, 133, 134, 135 and/or 136. According to various embodiments, a management module 131, 132, 133, 134, 135 and/or 136 reads rules stored on DBMS 150 via rules engine 141 and processes client request application requests associated with the respective workflow (e.g., category of the request). For example, the practitioner management module 133 processes client application requires for creating, reading, updating or deleting practitioner records.

At 605, validation engine 166 verifies that the container identifier information matches data stored on DBMS 150.

At decision block 612, the outcome of the validation process is determined. If the scanned or entered information does not match information stored on DMBS 150, then validation engine 166 returns a failed or disapproved value to the caretaker client device 110-1 application indicating that the action is not permitted (e.g., container identifier information is not located on the database) at 606. In some embodiments, the reception of the failed or disapproved value received at the caretaker client device 110-1 to display a message to the user indicating the validation failure. Such failure can be communicated by caretaker client device 110-1 audibly, e.g., by a noise or voice recording being played through speaker 122, by a tactile notification, e.g., by oscillator 123 vibrating in a certain pattern, visually, e.g., by displaying a message on display 168, or by combinations of the foregoing.

If the container identifier information matches data stored on DBMS 150 (e.g., the mother has entered and stored information prior to the caretaker scan or manual entry), i.e., validation passes, then at 607 the container identifier information is updated to reflect a check in date on management server.

At 608, in response to receiving the check-in date, management server 130 suggests a storage location for the container received by the caretaker, e.g., freezer or refrigerator, to list only a few possibilities. In various embodiments, management server 130 is configured to make additional suggestions for the management of milk containers. For example, management server 130 may suggest a container storage location, feeding order of the container, placement of the container in the storage location, or any other suggestion for the management of a container as would be understood by one of ordinary skill in the art.

At decision block 611, a determination is made as to whether a change was made to the storage location. For example, a nurse or other practitioner using the caretaker client device 110-1 may be prompted to confirm that the container was stored as suggested by the management server 130 or if the container was stored elsewhere. If the caretaker did not change the suggested storage location, then the receive workflow ends at 610.

If the caretaker changed the suggested storage location, e.g., by selecting a different location from a number of locations available to be selected on the caretaker client device 110-1 or by scanning an identifier associated with a different storage location, then the expiration date calculated based on the suggested storage location will change accordingly at 609. For example, in some embodiments, the caretaker client device 110-1 application updates the expiration date of the received container via expiration engine 167, which 167 reads rules stored on DBMS 150 via management server 130 and updates the expiration of a container based on those rules. In various embodiments, expiration engine 167 may interact with the validation engine 166. For example, if a container needs to validate data as part of updating the expiration date. Following update of the expiration date at 609, if necessary, the receive workflow ends at 610.

As noted above, in various embodiments, the container identifiers may be represented in a 1D barcode identifier (e.g., code-128, code-39, etc.), 2D barcode identifiers (e.g., QR codes, etc.), radio frequency identifiers (e.g., RFID), beacon-based identifiers, NFC tags, Bluetooth identifiers, or any suitable representation that may be identified using an image, scanning, or interrogating a device or object as described above. In various embodiments, represented identifiers may apply to bin identifiers (e.g., an identifier on a bin to store containers of a mother, her infants or to store donor or formula feeds) or an infant identifier (e.g., an identifier on an infant in the unit to uniquely identify the infant from other infants). In some embodiments, the container may contain any representative visual, electronic and/or suitable means on the label of a container that may be scanned or read, such that the representation corresponds to container identifiers stored on system 100. For example, a container label may not visually show an expiration or fortification identifier information. In this example, when the label is identified (e.g., read by system 100), expiration and/or fortification is returned to the user. In some embodiments, the caretaker client device 110-1 application is configured to show container identifier information to the user when a container, bin, or infant label identifier is read by client device 110.

Figure 7:
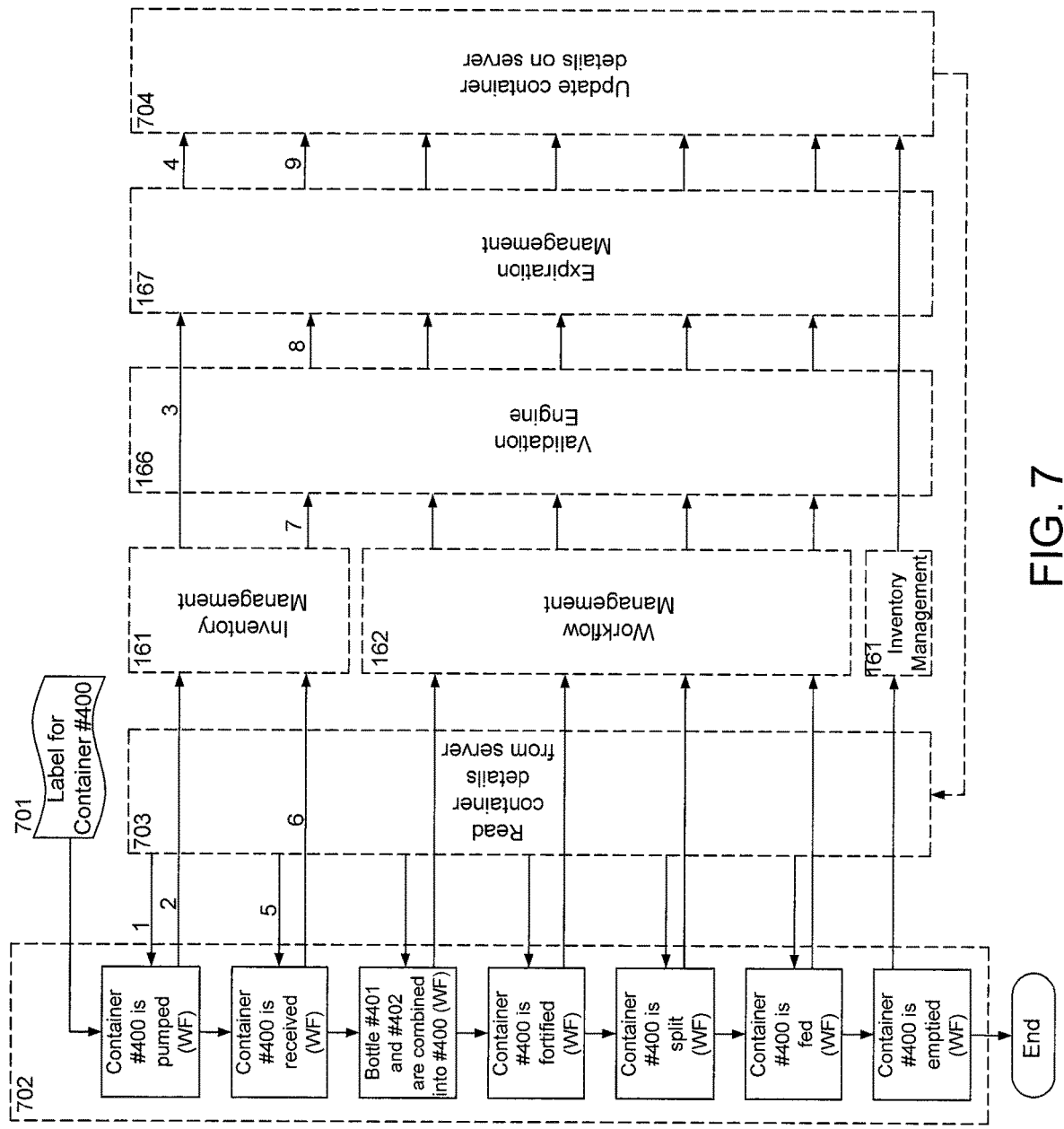
FIG. 7 is a diagram illustrating example workflow processes of the system in FIG. 1A-1E in accordance with some embodiments of the present disclosure.

FIG. 7 is a diagram illustrating one example of workflow processes of the system 100 illustrated in FIG. 1A-1C, in accordance with some embodiments of the present disclosure. As described above, system 100 is configured to eliminate the need for relabeling containers throughout the performance of various workflow processes.

At 701, a container is labeled. In some embodiments, the container is labeled before additional subsequent workflows may be performed; however, one of ordinary skill in the art will understand that, in some embodiments, certain other workflows can be performed prior to or concurrent with the labeling of a container.

As shown in FIG. 7, example workflow requests are identified at 702 (e.g., pumping, receiving, fortifying, and others). For any given workflow request, the caretaker identifies the container by scanning, reading, or interrogating the container label. In some embodiments, as shown in FIG. 7, inventory management module 161 of caretaker client device 110-1 processes user input for any inventory related workflow request 702 (e.g., container pumped, container received, container discharged/emptied, etc.), then updates user interface 168 with the processed data. In various embodiments, as shown in FIG. 7, workflow management module 162 processes user input for any workflow related workflow request 702 (e.g., combining a container, fortifying a container, splitting a container, feeding, etc.), then transmits the updates to management server 130. According to various embodiments, as shown in FIG. 7, inventory management module 161 and workflow management module 162 may interact with validation engine 166 to verify that valid data is being processed and returned, as discussed above. In some embodiments, inventory management module 161 and workflow management module 162 may interact with expiration engine 167 to update the expiration of a container based on the workflow request 702.

At 704, the container identifier information is updated on DBMS 150 via management server 130 in response to receiving the data processed and transmitted by caretaker client device 110-1. In various embodiments described above, container identifier information is updated on the server obviating the need to relabel the container.

Figure 8:
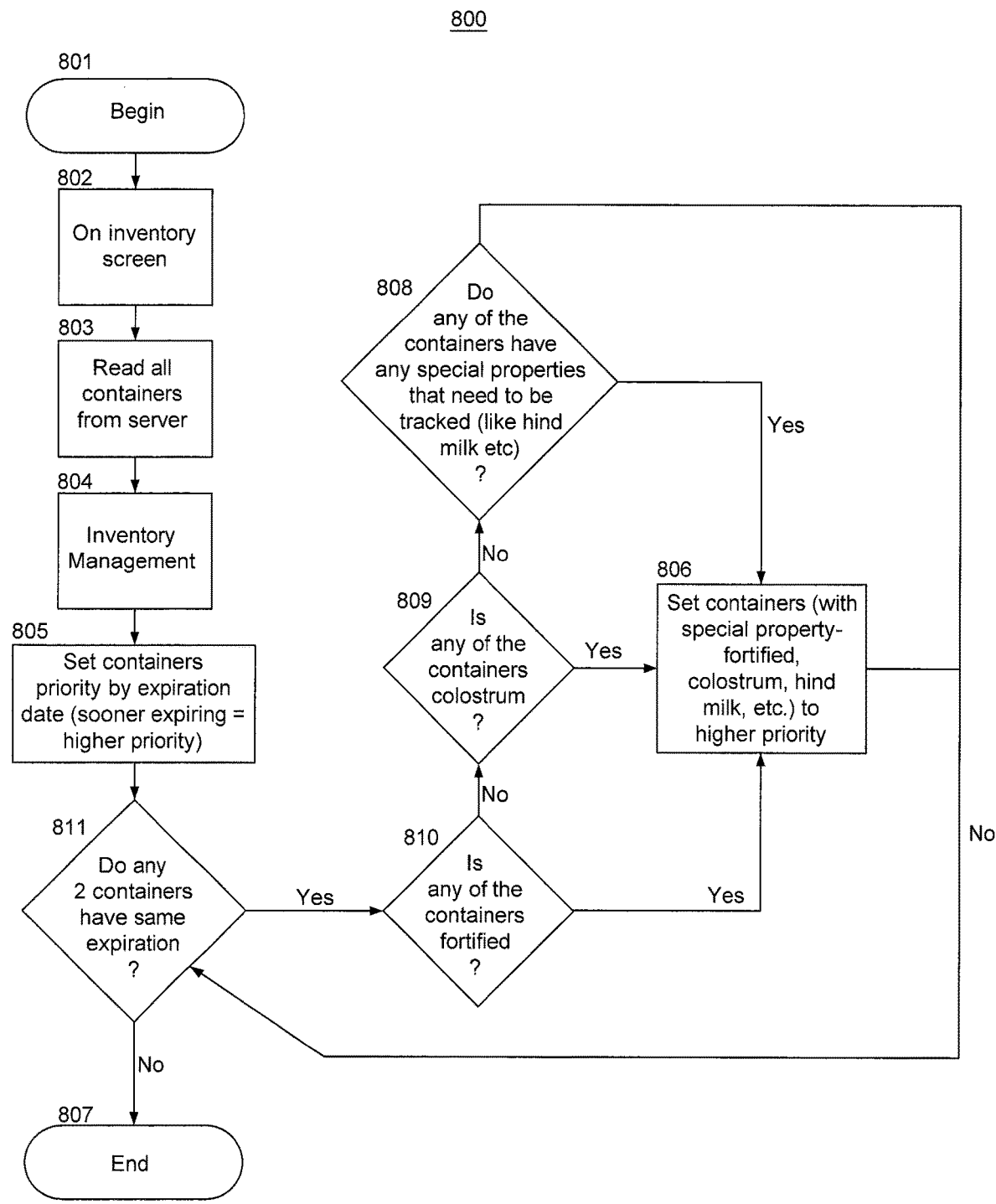
FIG. 8 is a flow diagram illustrating an example first-in first-out calculation process in accordance with some embodiments of the present disclosure.

FIG. 8 is a flow diagram illustrating one example of a FIFO calculation process 800 in accordance with some embodiments of the present disclosure. Conventional flow processes with milk containers required a caretaker to maintain a sequential number system by manually writing the sequential numbers on the container before placing them in order inside a refrigerator or deep freezer. A typical conventional arrangement may be that the newest (e.g., expiration date furthest in time to expiring) containers were placed toward the back and the oldest containers (e.g., expiration date closest in time to expiring) were placed toward the front. A problem associated with conventional flow processes is that containers with upcoming expiration dates could be inadvertently misplaced by the caretaker resulting in unused expired milk. In various embodiments, system 100 maintains container identifier information (e.g., expiration date, container thawed status, container fortified status, milk type (e.g., colostrum, hind, fore, etc.), etc.). System 100 is configured to suggest a FIFO order of milk bottles, thereby maximizing the duration of availability of unexpired milk.

At 801, the FIFO calculation process begins.

At 802, an inventory screen is presented to a user on user interface 168 of caretaker client device 110-1 for displaying and processing of milk containers. The user interface may display several pieces of information like identifier information, expiry information, details about fortification, properties like colostrum, hind milk, fore milk, etc., details about pumping, etc.

At 803, information concerning each milk container is read from management server 130. For example, in some embodiments, caretaker client device 110-1 requests the container information concerning all containers associated with a specific mother or feeding order. As described elsewhere herein, a nutrition or feeding order sets for a specific nutrition regimen that is to be followed by a mother for her child or children. Unlike some conventional milk management systems that associate a specific bottle or container with a certain mother and child, the disclosed systems and methods perform milk management by associating containers with a mother and feeding order. Such association advantageously provides enhanced flexibility compared to conventional systems. For example, if a mother has multiple children that are in a NICU, then each child may be assigned a specific feeding order (nutrition regimen), which can be the same feeding order or different from one another. If the feeding orders are the same, then a container having milk that matches the feeding order can be used for either child, which improves the freshness and retention of the pumped milk.

At 804, inventory management module 161 of caretaker client device 110-1 processes user input for any inventory related workflow (e.g., inventory display, container transfer, emptying a container, receiving a container, discharging a container, etc.). Inventory management module 161 may be configured to interact with validation engine 166 to ensure valid data is being processed and returned. In some embodiments, inventory management module 161 may interact with expiration engine 167 of caretaker client device 110-1 when there is a workflow or process that updates an expiration as part of the action/task. For example, if a container is being transferred from a first storage location to a second storage location (e.g., from a refrigerator to a freezer), then validation engine 166 will ensure that the container was not previously thawed and has not expired. In this example, the container expiration date is required to be updated from a date for a refrigerator (e.g., approximately 72 hours) to an expiration date for a freezer (e.g., approximately 6 months). The expiration update will be processed by expiration engine 167. The updated information is then transmitted back to management server 130 for storage in DBMS 150.

At 805, a container priority is set based on the expiration date. For example, the sooner in time that the expiration date is, the higher priority that will be assigned to the container for use. Such priority value may also be saved in DBMS 150 such that the priority value is associated with a particular container.

At 806, the containers are updated with additional container identifier information that may affect priority and/or expiration (e.g., fortification, colostrum milk, hind milk, etc.) determined at decision blocks 808-810. At decision block 811, if at least no two containers have the same expiration date, at 807, the FIFO calculation process 800 ends following assignment of priority to the container based on expiration date and/or additional container identifier information.

In various embodiments, system 100 is configured to provide an automated method to calculate the appropriate ingredient quantities (e.g., volumes, units, etc.) that are to be mixed as described in the FIFO calculation process above. In some embodiments, an algorithm is provided for calculating volumes for feeding order management in the form of a feeding order management module 136 resident on management server 130, although one of ordinary skill in the art will understand that feeding order management module 136 can be resident on other devices (e.g., caretaker client device 110-1) and/or distributed across a plurality of devices (e.g., management server 130 and caretaker client device 110-1). Feeding order management module 136 is configured to process user input for any nutrition order related tasks (e.g., set nutrition order, read nutrition order, etc.). As will be disclosed below, a nutrition or feeding order may refer to the fortification, quantity, and preparation of a container. Order management module 136 may interact with validation engine 166 resident on caretaker client device 110-1 to ensure valid data is processed and returned to management server 130. Order management module 136 on management server 130 also may interact with expiration engine 167 on caretaker client device 110-1 if there is a need (e.g., a workflow process requires) to update an expiration date for a container. In various embodiments, management server 130 comprises a feeding order management module 136 configured to process client request for creating, reading, updating, and/or deleting feeding order records. A workable example of an algorithm to calculate volumes for order management (e.g., how many fortifiers (Z) and how much milk is needed "N" feeds) follows.

In some embodiments, the following algorithm is a linear programming algorithm with the following 7 variables—
A=base caloric value of milk (e.g., it is globally assumed to be at 20 cal/oz);
B=extra caloric value of milk (e.g., 2 cal/oz for example, or milk is to be fed to the baby at 2 cal/oz);
C=caloric value of the fortifier (e.g., a fortifier can add 2 cal/oz when added to required amount (E));
D=minimum quantity of fortifier that can be used (e.g., 1 packet, ½ TSP, etc.)
E=amount of milk needed to use this minimum quantity of fortifier (e.g., of variables C, D, and E→1 packet of fortifier when added to 5 oz of milk will increase the caloric value of milk by 2 cal/oz);
F=required milk volume per feed
N=how many feeds is the nurse preparing
Hard Constraints
The hard constraints in this above calculation are D and E (e.g., you can't use ½ packet of milk in 2.5 oz of milk). This is to ensure that the right amount of fortifier is always used as prescribed.
Simple Case Solution→when B=C For example, consider the case if extra caloric value required:
(B)=2 cal/oz and caloric value of the fortifier; and
(C)=2 cal/oz when added to 5 oz of milk
Find the amount of milk needed (X)=N*F
(e.g., this is the minimum amount of milk we need to fortify)
Find the next multiple of E higher than X (next higher multiple) (Y)
(e.g., Y=Next higher multiple (X,E))
Y is the milk needed to prepare N feeds. This might be higher than X, which is the case of fortifying more milk than needed.
Number of fortifiers (packets, Tsp's, etc.) needed (Z)=Y/E
Complex Case Solution→when B is not equal to C
For example, consider the case if extra caloric value required:
(B)=2 cal/oz and caloric value of the fortifier; and
(C)=1 cal/oz when added to 5 oz of milk.
Find the exact amount of milk needed (X)=N*F
Find the next multiple of E higher than X (next higher multiple) (Y)
(e.g. Y=Next higher multiple (X,E))
Y is the milk needed to prepare N feeds. This might be higher than X, which is the case of fortifying more milk than needed.
Find the least common multiple of B,C (M)
(e.g., M=LCM(B,C))
Number of fortifiers (packets/TSPs etc.) needed (Z).
(e.g., Z=M*(Y/E))
A workable example of an algorithm to calculate updated expiration dates/times follows. Calculate expiration in refrigerator (Container A)
(e.g., X=pumped_time_A+refrigerator_expiration_threshold)
Calculate expiration in freezer (Container A)
(e.g., X=pumped_time_A+freezer_expiration_threshold)
Calculate expiration for thawing (Container A)
(e.g., E=min(current_bottle_expiration, current_time_A+thaw_expiration_threshold))
Calculate expiration for fortifying (Container A)
(e.g., E=min(current_expiration_A, current_time_A+fortify_expiration_threshold))
Calculate expiration for combining bottles (e.g., Containers A and B are combined into container C)
(e.g., E=min(current_expiry_A, current_expiry_B, current_expiry_C))

As described above, system 100 is configured to update container identifier information stored in DBMS 150. In some embodiments, when an infant is transferred between units (e.g., NICU, postpartum hospital, milk donor bank, child day care), system 100 updates DBMS 150 container identifier information for the respective infant. For example, provider identifier information is updated in DBMS 150 when an infant is transferred from one unit to another unit. In various embodiments, updated container identifier information is accessible to users of caretaker client device 110-1 associated with the unit at the location the infant is transferred. For example, containers identifier information reflects the infant's new unit following initiation of a transfer by a caretaker.

In various embodiments, system 100 is configured to provide a log for each workflow performed on a container. For example, if a container is delivered to a mother for feeding, that action is logged by system 100 and stored in DMBS 150. In some embodiments, workflow log information may be stored in an additional data store (not shown).

Patient Engagement

As described above, while lactation is a natural process, pumping milk away from the baby is an unnatural process due to the lack of stimuli (e.g., infant's touch, infant's sounds, etc.). The absence of such natural stimuli makes it harder for mothers to lactate and produce a sufficient quantity of milk for their infants. In various embodiments, system 100 is configured to provide a secured means of sharing images, vides, and/or audio (e.g., media) between caretakers and mothers. In some embodiments, media may be shared and/or displayed on a mother client device 110-2. Sharing media between caretakers and mothers, digitally bridges the gap of missing stimuli. In some embodiments, system 100 is configured to provide real-time communication between caretakers and mothers via client device(s) 110. Real-time communication may include text, video, audio messaging, and/or calling services. In various embodiments, media and communications may be shared over an encrypted, unencrypted, secured, or unsecured line. It should be appreciated, that media and communications can be shared by various methods suitable of ensuring HIPPA compliance or other required compliances as would be understood by one of ordinary skill in the art.

Tracking and Analytics

As described above, tracking shelf life requires a caretaker to manually determine order and location. In addition, caretakers are limited to manual means of tracking the total available milk for infants. If a mother's milk runs out, caretakers resort to donor milk or formula to feed her infant. Not all infants are suited for donor/formula feeding, which creates several health issues for the infant, such as necrotizing colitis and retinopathy of prematurity. In addition, caretakers need to track when a unit is running out of milk. When a unit is running out of milk caretakers need a means of notifying mothers to produce additional milk. Each of these issues are addressed in the present disclosure.

In various embodiments, system 100 is configured to keep track of the expiration date of a container throughout the lifecycle of the container (e.g., at home or at the unit). As described above, the expiration date may be updated based on the workflow (e.g., action) performed on the container. In some embodiments, system 100 is configured to keep track of the total available milk for the infant by calculating, based on volume inputted by the mother via client device 110, and the volume recorded in the feeding order of the infant. System 100 maintains a global state of the container inventory and sends notifications to mothers and caretakers when the container inventory has reached a predetermined low state at the unit. In some embodiments, system 100 is configured to set reminders notifying mothers at a predetermined time and/or when container inventory has reached a predetermined low state. In some embodiments, notifications may include if the mother is recording her pumping session after a predetermined time following commencement of the pumping session. In various embodiments, system 100 provides real-time dashboards for caretakers to keep track of mothers' production patterns via text, visual interfaces, or any suitable means of determining pumping patterns as would be understood to one of ordinary skill in the art. In some embodiments, system 100 is configured to provide notifications when a mothers' pumping pattern shows an irregular or abnormal pattern.

Figure 9:
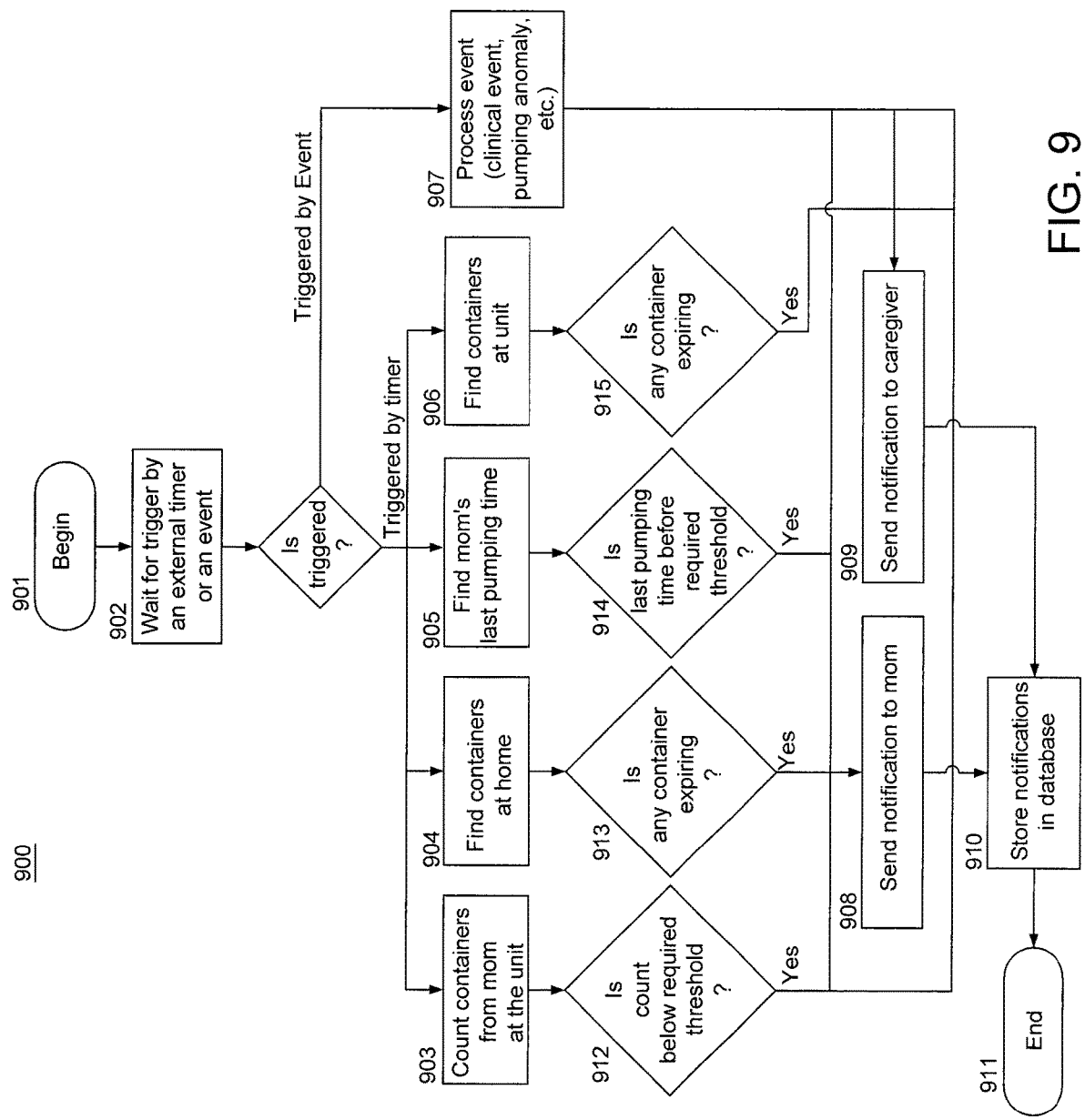
FIG. 9 is a flow diagram illustrating an example notifications engine process in accordance with some embodiments of the present disclosure.

FIG. 9 is a flow diagram illustrating an example notifications engine process 900 in accordance with some embodiments of the present disclosure. In some embodiments, notifications engine 137 resides at management server 130; however, one of ordinary skill in the art will understand that notifications engine 137 can be located at another device (e.g., at a caretaker client device 110-1 or at mother client device 110-2) or can be distributed across multiple devices (e.g., management server 130 and/or mother and/or caretaker client devices 110). Notifications engine 137 is configured to read rules from rules engine 141 and generate one or more notifications for alerting a user of caretaker client device 110-1 and/or mother device. Notifications engine 137 may use rules from rules engine 141 to process client workflow requests or scheduler engine 140 requests. Notifications engine 137 is configured to create, read, update, delete and/or send notifications to patients (e.g., mothers) and practitioners (e.g., caregivers) based on workflow or scheduler engine 140 requests. For example, a schedule engine 140 requests may include a container expiration date/time event. In this example, notifications engine 137 will process the container expiration date/time event from the scheduler engine 140 by sending a notification to the caregiver.

Referring back to FIG. 9, at 901, the notifications engine process begins.

At 902, a predetermined time or event as determined by the caretaker, mother, or the unit may be triggered. For example, if the container inventory is low at the unit, system 100 may trigger an event in notifications engine 137 via scheduler engine 140. In the event that the trigger is driven by an event (e.g., a workflow step/action), notification engine 137 will process the event, at 907, and send a notification about the event to a caregiver, at 909. If the event is a time based event (e.g., initiated by scheduler engine 140), then the event is verified at 903, 904, 905, and/or 906. For example, scheduler engine 140 may establish a predetermined time for reviewing the container inventory at a unit or home. In this example, if at the time scheduler engine 140 initiates a review, notifications engine 137 will verify if the container inventory has reached a predetermined low state limit at decision block 912. If a predetermined low state limit is reached, notifications engine 137 will send a notification to the mother, at 908, or the caregiver, at 909, based on the type of trigger that was initiated. A container inventory low state may initiate a notification to be sent to the caregiver. In some embodiments, a container set to expire at the home may initiate a notification to be sent to the mother at decision block 913. In various embodiments a notification may be sent to the mother if the pumping time is exceeded at decision block 914. In some embodiments, a notification may be sent to the caregiver when a container has expired at decision block 915. At 910, notifications are logged in DBMS 150 via rules engine 141 and database connection interface 143. The notifications engine process 900 ends at 911.

Figure 10:
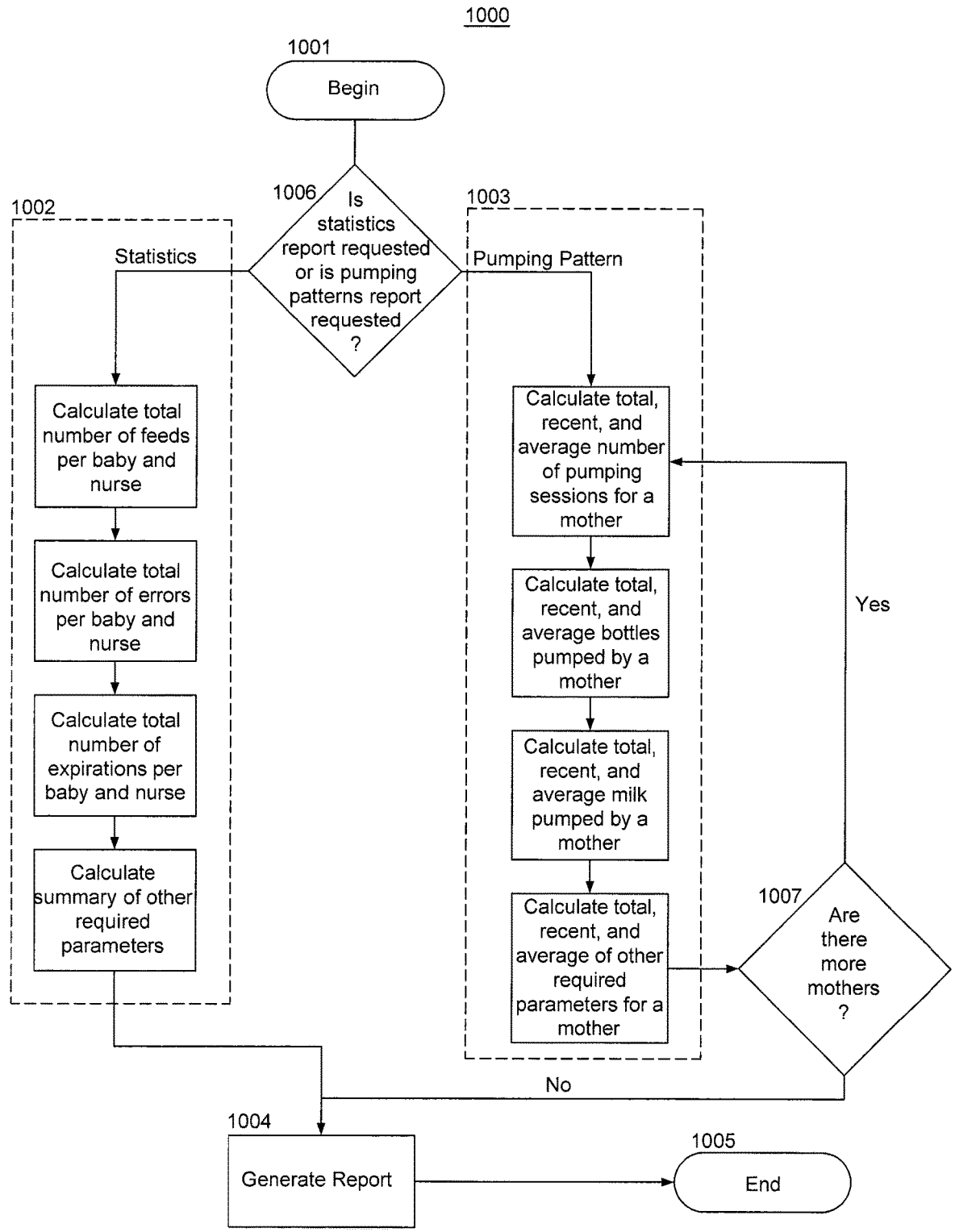
FIG. 10 is a flow diagram illustrating an example reporting engine process in accordance with some embodiments of the present disclosure.

FIG. 10 is a flow diagram illustrating an example reporting engine process 1000 in accordance with some embodiments of the present disclosure. In some embodiments, system 100 provides information about the production pattern of the lactating mother to one or more lactation experts. If a problem with the pattern is discovered, then lactation experts can intervene in a timely manner and provide appropriate counseling. Using a chat platform included in a system consistent with some embodiments of the disclosure, mothers can reach out to lactation experts in real-time regarding any concerns or questions about breastfeeding or production patterns. In some embodiments, the consumption patterns of infants are shared with their parents. In some embodiments, machine-learning prescriptive analytics on these consumption patterns can identify possible health issues with the infants, based on historical data. In various embodiments, system 100 provides a real-time dashboard that provides information concerning pumping patterns and statistic reports in a visual or text interface.

Although communications techniques embodiments have been described herein to verify the identity of mothers, infants, milk, containers, syringes, and other associated devices, it should be understood that, in alternative embodiments, other verification techniques, hardware, and software may be used in a system consistent with the invention. For example, in one embodiment, biometric data (e.g., fingerprinting or retina scanning) may be used to verify identity. Additionally, non-biometric techniques, such as a password, encryption key, data file, hardware token, or other non-biometric scheme, may be employed. In some embodiments, a combination of one or more biometric verification techniques and one or more non-biometric techniques is used.

Referring back to FIG. 10, reporting engine 139 is configured to read rules from rules engine 141 and process client workflow requests and/or scheduler engine 140 requests. Reporting engine 139 creates, reads, updates, and/or deletes report and dashboard information as described above. The reporting engine process begins at 1001. At decision block 1006, in the event that a statistics report is requested via a real-time dashboard, example statistic calculations 1002 for generating a report may include number of feeds per infant and nurse, number of errors per infant and nurse, number of expirations per infant and nurse, summary of other parameters (like summary of feedings by baby or summary of errors by nurses, etc.), and/or any additional information to determine statistics used for tracking milk management as would be understood by one of ordinary skill in the art. At decision block 1006, in the event that a pumping pattern report is requested, example pumping pattern calculations 1003 for generating a report may include pumping session information, container pumping information, milk production, additional parameters (like information grouped by dates or time-periods, etc.), donor production (e.g., more than one mother), and/or any additional information to determine pumping patterns as would be understood by one of ordinary skill in the art. At decision block 1007, the pumping pattern calculations 1003 may be calculated where pumping patterns are being determined for more than one mother. At 1004, a report is generated for display on client device 110 via a real-time dashboard. At 1005, the reporting engine process is complete following generation of the report.

The present invention can be embodied in the form of methods and apparatus for practicing those methods. The present invention can also be embodied in the form of program code embodied in tangible media, such as secure digital ("SD") cards, USB flash drives, diskettes, CD-ROMs, DVD-ROMs, Blu-ray disks, hard drives, or any other non-transitory machine-readable storage medium, wherein, when the program code is loaded into and executed by a machine, such as a computer, the machine becomes an apparatus for practicing the invention. The present invention can also be embodied in the form of program code, for example, whether stored in a storage medium, loaded into and/or executed by a machine, or transmitted over some transmission medium, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits.

It may be emphasized that the above-described embodiments, are merely possible examples of implementations, and merely set forth a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

While various embodiments have been described, it is to be understood that the embodiments described are illustrative only and that the scope of the subject matter is to be accorded a full range of equivalents, many variations and modifications naturally occurring to those of skill in the art from a perusal hereof.

What is claimed is:

1. A system, comprising: a first device, the first device including:
   a non-transitory storage medium; and
   a processor communicatively coupled to the non-transitory storage medium, the processor configured to:
      receive first data from a second device, the first data describing milk disposed in a first container, the first container having a first identifier associated therewith, wherein the first identifier links the first container to a mother who provided the milk disposed in first the container;
      associate the first data with a first feeding order in a data structure stored in a database, the first feeding order describing a first nutrition regimen; and
      identify a first child and a second child associated with the mother and with the first feeding order.

2. The system of claim 1, wherein the processor is further configured to:
   receive a message from a third device, the message including at least the first identifier; and
   cause at least a portion of the first data stored in the data structure in the database to be transmitted to the third device.

3. The system of claim 1, wherein the first data includes a date and time that the milk disposed in the first container was pumped.

4. The system of claim 3, wherein the processor is further configured to execute an expiration engine for calculating an expiration date of the milk disposed in the first container based at least in part on the first data stored in the data structure in the database.

5. The system of claim 4, wherein the processor is further configured to cause an alert identifying an approaching expiration date to be transmitted to at least one of the second device and the third device.

6. The system of claim 1, wherein the processor is further configured to generate the first identifier in response to receiving a request from at least one of the second device and a third device.

7. The system of claim 6, further comprising a printer configured to print a label including a representation of the first identifier.

8. The system of claim 1, wherein the processor is configured to:
calculate an amount of at least one fortifier to be added to the milk disposed in the first container based on the first feeding order; and
cause a message, including the amount of the at least one fortifier to be added to the milk disposed in the first container, to be transmitted to the third device.

9. The system of claim 1, wherein the processor is further configured to:
receive second data from the second device, the second data describing milk disposed in a second container and including a date and time that the milk disposed in the second container was pumped, the second container having a second identifier associated therewith; and
associate the second data with the first feeding order in the database.

10. The system of claim 9, wherein the processor is further configured to:
analyze a pumping pattern based at least in part on the first data and the second data; generate an alert to pump milk; and
cause the alert to pump milk to be transmitted to at least one of the second device and a third device.

11. The system of claim 1, wherein the processor is further configured to associate when the milk disposed in the first container is used to feed the first child or the second child and an identifier of a caretaker who feeds the first child or the second child with the first data in the data structure.

12. The system of claim 11, wherein the processor is further configured to store data concerning a total quantity of stored milk in the data structure.

13. The system of claim 1, wherein the processor is further configured to:
receive second data, the second data identifying a refrigeration state of the milk disposed in the first container; and
determine a first expiration date for the milk disposed in the first container based on the refrigeration state.

14. The system of claim 13, wherein the processor is further configured to:
receive third data, the third data identifying a change in the refrigeration state of the milk disposed in the first container, and
update the first expiration date of the milk disposed in the first container based on the change in the refrigeration state.

15. A method, comprising the steps of:
providing a system comprising a first device and a second device, wherein the first device include a non-transitory storage medium and a processor communicatively coupled to the non-transitory storage medium;
receiving, by the processor, first data from the second device, the first data describing milk disposed in a first container, the first container having a first identifier associated therewith, wherein the first identifier links the first container to a mother who provided the milk disposed in the first container;
associating, by the processor, the first data with a first feeding order in a data structure stored in a database, the first feeding order describing a first nutrition regimen; and
identifying, by the processor, a first child and a second child associated with the mother and with the first feeding order.

16. The method of claim 15, further comprising the steps of:
receiving, by the processor, a request from a third device, the request including at least the first identifier; and
causing, by the processor, at least a portion of the first data to be transmitted to the third device.

17. The method of claim 15, further comprising the steps of:
calculating, by the processor, an expiration date of the milk disposed in the first container based at least in part on the first data; and
causing, by the processor, an alert identifying an approaching expiration date to be transmitted to at least one of the second device or a third device.

18. The method of claim 15, further comprising the steps of:
receiving, by the processor, a request from at least one of the second device or a third device; and
generating, by the processor, the first identifier in response to receiving the request from at least one of the second device and the third device.

19. The method of claim 15, further comprising the steps of:
calculating, by the processor, an amount of at least one fortifier to be added to the milk disposed in the first container based on the first feeding order; and
causing, by the processor, a message, including the amount of the at least one fortifier to be added to the milk disposed in the first container, to be transmitted to a third device, the third device associated with a caretaker.

20. The method of claim 15, further comprising the steps of:
receiving, by the processor, second data from the second device, the second data describing milk disposed in a second container and including a date and time that the milk disposed in the second container was pumped, the second container having a second identifier associated therewith;
associating, by the processor, the second data with the first feeding order stored in the database;
analyzing, by the processor, a pumping pattern based at least in part on the first data and the second data;
generating, by the processor, an alert to pump milk; and
causing, by the processor, the alert to pump milk to be transmitted to at least one of the second device or a third device.

* * * * *